United States Patent [19]
Sakurai et al.

[11] Patent Number: 5,076,276
[45] Date of Patent: Dec. 31, 1991

[54] ULTRASOUND TYPE TREATMENT APPARATUS

[75] Inventors: Tomohisa Sakurai; Tetsumaru Kubota; Hitoshi Karasawa, all of Hachioji; Tatsuya Kubota, Sagamihara; Yuichi Ikeda, Hachioji; Mitsumasa Okada, Hachioji; Toshihiko Suzuta, Hachioji; Hideo Nagazumi, Hachioji; Kazuya Hijii, Hachioji; Masahiro Kudo, Hachioji; Hiroaki Kagawa, Hachioji; Kenji Yoshino, Tama; Tadao Hagino, Yokohama, all of Japan

[73] Assignee: Olympus Optical Co., Ltd., Tokyo, Japan

[21] Appl. No.: 573,673

[22] Filed: Aug. 24, 1990

[30] Foreign Application Priority Data

Nov. 1, 1989 [JP] Japan .................... 1-285700
Nov. 7, 1989 [JP] Japan .................. 1-129854[U]
Nov. 7, 1989 [JP] Japan .................... 1-289652

[51] Int. Cl.⁵ ................................ A61B 8/00
[52] U.S. Cl. ................... 128/660.01; 128/24 AA; 606/128; 73/861.18
[58] Field of Search .................. 128/660.01, 24 AA; 604/22, 27; 73/861.18; 606/128

[56] References Cited

U.S. PATENT DOCUMENTS

| | | | |
|---|---|---|---|
| 4,526,571 | 7/1985 | Wuchinich | 128/24 AA |
| 4,587,958 | 5/1986 | Noguchi et al. | 128/24 AA |
| 4,660,573 | 4/1987 | Brumbach | 73/861.18 |
| 4,750,488 | 6/1988 | Wuchinich et al. | 604/22 |
| 4,750,902 | 6/1988 | Wuchinich et al. | 604/22 |
| 4,783,997 | 11/1988 | Lynnworth | 606/128 |
| 4,827,911 | 5/1989 | Broadwin et al. | 128/24 AA |
| 4,844,080 | 7/1989 | Frass et al. | 128/660.01 |
| 4,897,079 | 1/1990 | Zaleski et al. | 604/22 |
| 4,922,902 | 5/1990 | Wuchinich et al. | 604/27 |

FOREIGN PATENT DOCUMENTS

| | | | |
|---|---|---|---|
| 0172067 | 7/1985 | European Pat. Off. | 606/128 |
| 0232678 | 8/1987 | European Pat. Off. | 606/128 |
| 0316796 | 11/1988 | European Pat. Off. | 606/128 |
| 882624 | 7/1953 | Fed. Rep. of Germany | 606/128 |
| 16834 | 6/1956 | Fed. Rep. of Germany | 606/128 |
| 1573805 | 11/1970 | Fed. Rep. of Germany | 606/128 |
| 3309881 | 9/1984 | Fed. Rep. of Germany | 606/128 |
| 3407958 | 11/1985 | Fed. Rep. of Germany | 606/128 |
| 3527586 | 11/1986 | Fed. Rep. of Germany | 606/128 |
| 3731482 | 4/1988 | Fed. Rep. of Germany | 606/128 |

OTHER PUBLICATIONS

Patent Abstract of Japan; Aug. 24, 1989, vol. 13, No. 384 (62-293148).
Patent Abstract of Japan; Jul. 17, 1989, vol. 13, No. 313, (62-256254).

*Primary Examiner*—Francis Jaworski
*Assistant Examiner*—George Manuel
*Attorney, Agent, or Firm*—Frishauf, Holtz, Goodman & Woodward

[57] ABSTRACT

An ultrasound type treatment apparatus includes an ultrasonic oscillation device for outputting an ultrasonic oscillation wave, a drive circuit for driving the ultrasonic oscillation device, a probe connected to the ultrasonic oscillation device to transmit that ultrasonic oscillation wave to an affected region of interest of a human being, a sheath formed around the probe, through which cooling medium is passed and a supply tank for supplying cooling medium to the sheath. In this treatment apparatus, an arithmetic operation circuit monitors a drive state of the ultrasonic oscillation device, a comparator is provided for receiving monitor information from the arithmetic operation circuit and for determining whether or not the supply of cooling medium to the sheath is normal and a controller is provided for stopping a drive of the ultrasonic oscillation device when the supply of the cooling medium is determined by the comparator as being not normal.

20 Claims, 21 Drawing Sheets

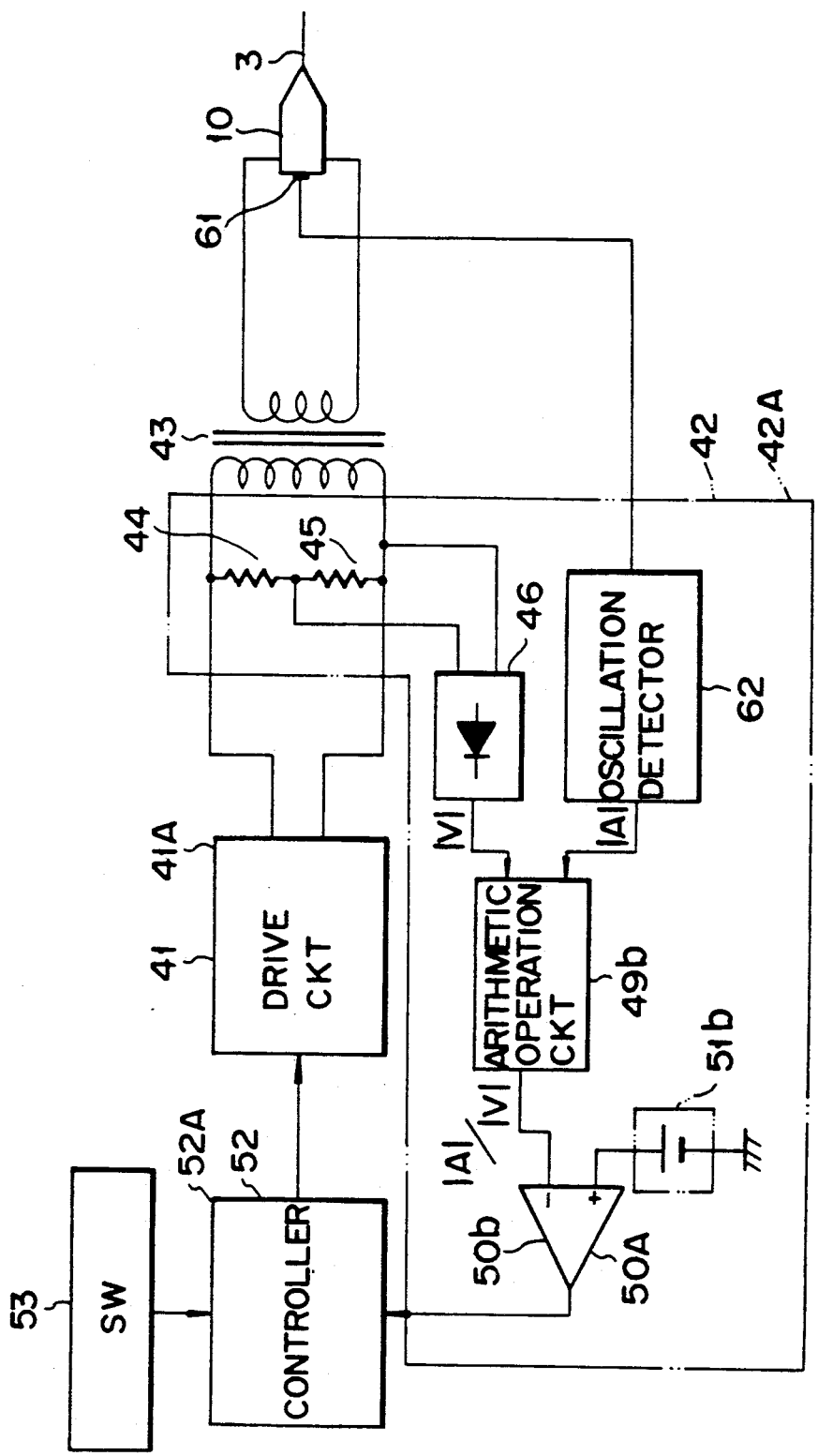
F I G. 6

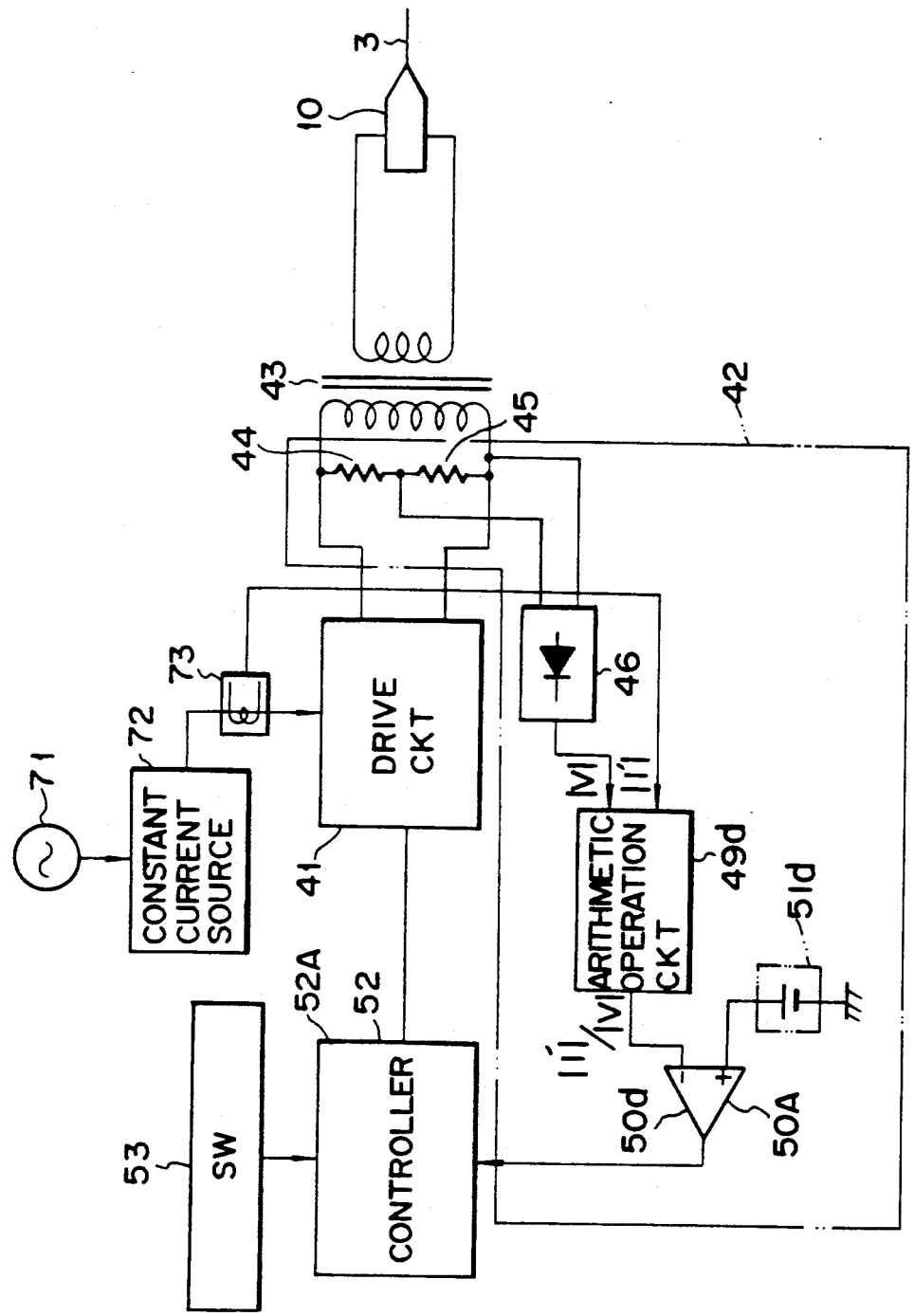
F I G. 10

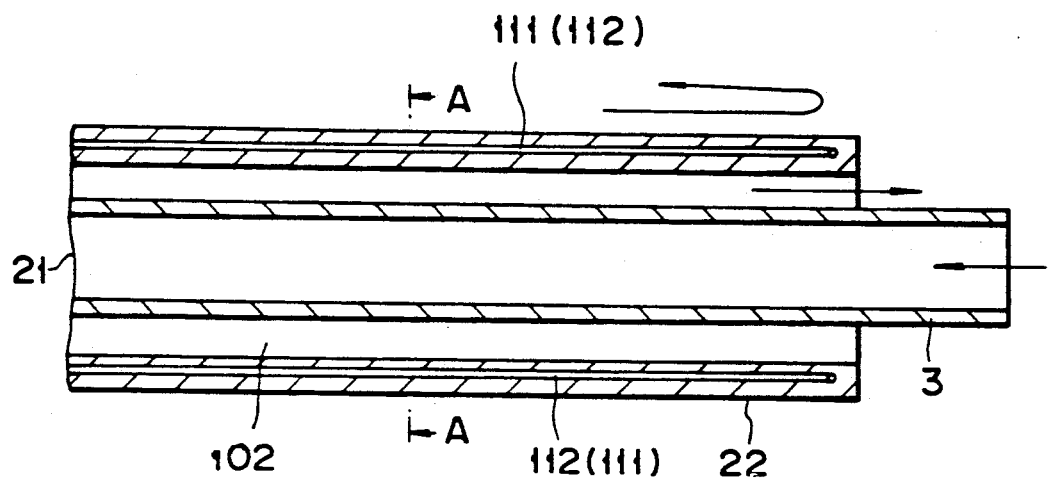
F I G. 30
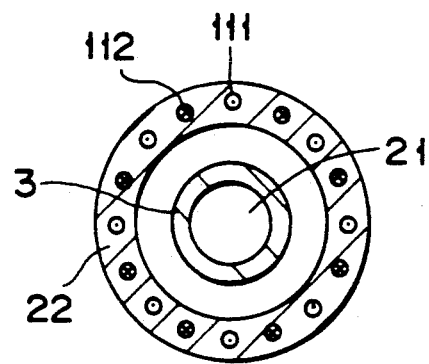
F I G. 31

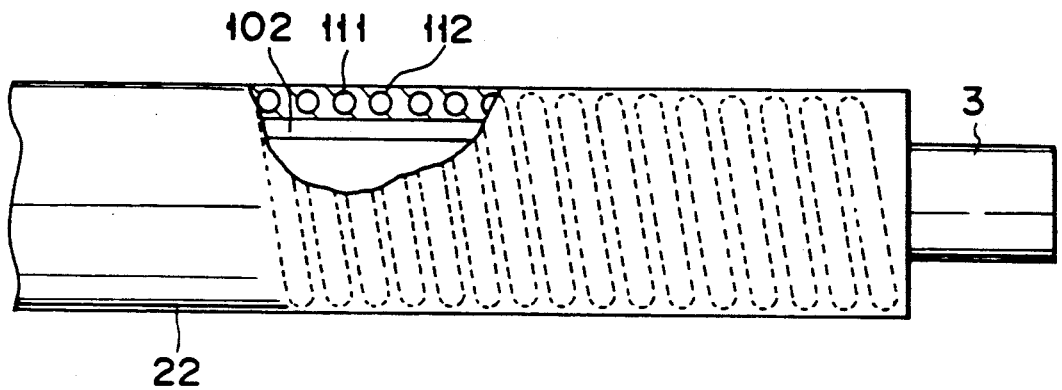
F I G. 32
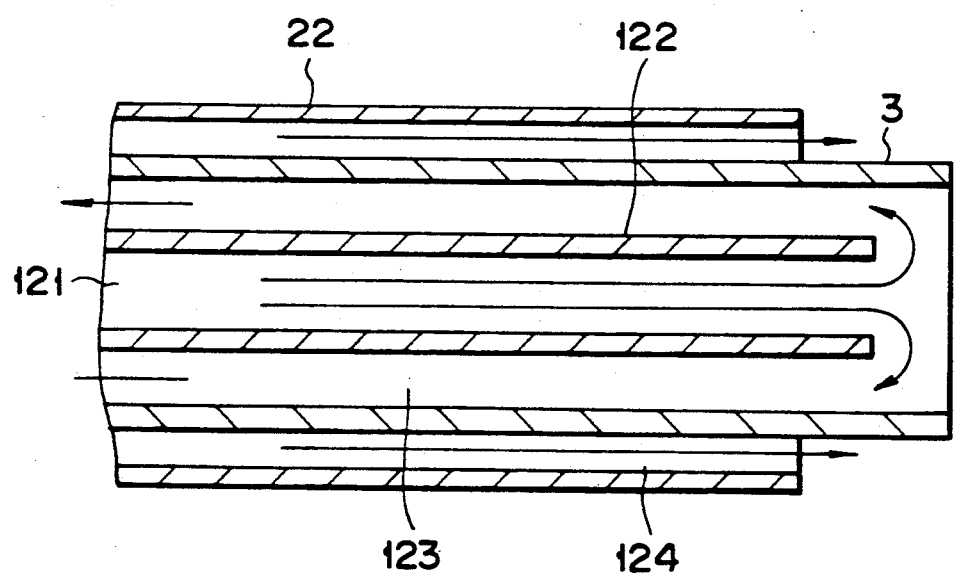
F I G. 33

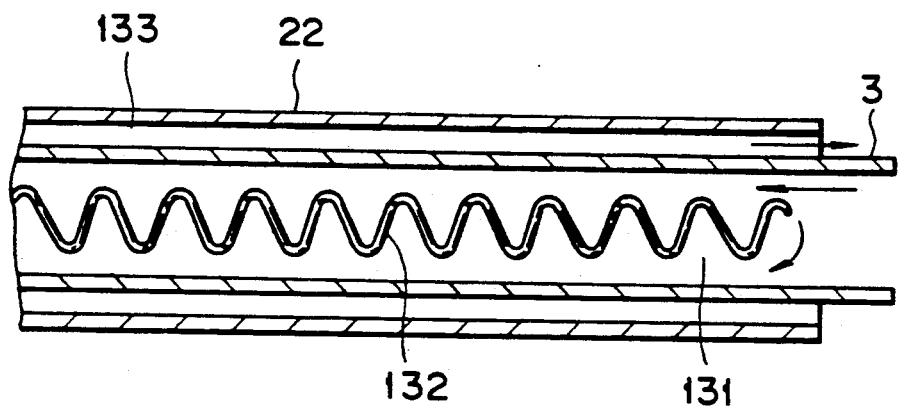
F I G. 37
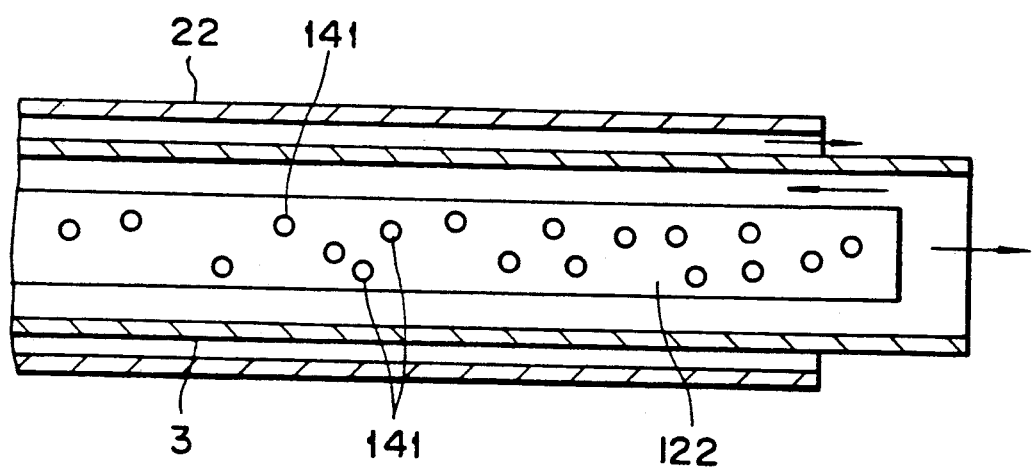
F I G. 38

ULTRASOUND TYPE TREATMENT APPARATUS

BACKGROUND OF THE INVENTION

1. Field of the Invention

The present invention relates to an ultrasound type treatment apparatus for resecting or emulsifying a living tissue or breaking down a stone with the use of an ultrasonic oscillation wave transmitted from an ultrasonic oscillation device.

2. Description of the Related Art

Generally, an ultrasonic type treatment apparatus includes an ultrasonic oscillation device and an ultrasonic wave transmitter for transmitting an ultrasonic oscillation wave of the ultrasonic oscillation device to a to be treated region of a human being. The treatment apparatus has been surgically employed to resect an affected region of a living tissue or break down a stone in a body cavity.

The treatment apparatus of this type uses a probe as an ultrasonic oscillation medium composed of a hollow tube. Upon the operation of the ultrasonic oscillation device an ultrasonic oscillation wave of the ultrasonic oscillation device is transmitted to the probe, producing a longitudinal oscillation wave and hence a strain at a node of the longitudinal oscillation wave. A temperature rise occurs at the probe due to the development of such a strain, there being a risk that a fatigue or a destruction will take place at the probe. If the probe is destroyed during the use of the treatment apparatus, then its fragments will be scattered around in the body cavity of a human being.

It has been common practice to cover a probe with a sheath and prevent a temperature rise in the probe with a cooling water stream run in the sheath.

There is a risk that a tank of cooling water will become empty in the use of the apparatus or a tube for supplying cooling water will be detached from the rest of the apparatus. In such a case, the probe is sometimes or rather often weakened or destroyed in the use of the apparatus.

SUMMARY OF THE INVENTION

It is accordingly the object of the present invention to provide an ultrasound type treatment apparatus which can initially prevent a temperature rise in an ultrasonic wave transmitter and achieve an added safety during use.

According to the present invention, there is provided an ultrasound type treatment apparatus comprising:

ultrasonic oscillation means for outputting an ultrasonic oscillation wave;

drive means for driving the ultrasonic oscillation means;

ultrasonic wave transmitting means, connected to the ultrasonic oscillation means, for transmitting the ultrasonic oscillation wave from the oscillation wave means to a affected region of interest of a human being;

communicating means formed around the ultrasonic wave transmitting means, through which cooling medium is passed; and supply means for supplying the cooling water to the communicating means, characterized by further comprising:

monitor means for monitoring a drive state of the ultrasonic oscillation means and outputting monitor information;

determining means for receiving the monitor information from the monitor means and for determining whether or not the supply of the cooling medium to the communication means is normal; and control means for stopping a drive of the ultrasonic oscillation means when the supply of the cooling medium is not normal.

At the time of normal driving, it is possible to prevent a temperature rise in the ultrasonic oscillation device by supplying the cooling medium into the cooling medium communicating means and to, if the supply of the cooling medium is not done, detect it and stop the driving of the ultrasonic oscillation means. It is thus possible to prevent a temperature rise in the ultrasonic wave transmitter and to provide a higher degree of safety.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 6 is a schematic view showing a major section of an ultrasound type treatment apparatus according to a second embodiment of the present invention;

FIG. 10 is a schematic view showing a fourth embodiment of the present invention;

FIGS. 25 to 30, each, show a different modification showing a distal end portion of the apparatus above;

FIG. 31 is a side view, in cross-section, taken along line A—A of FIG. 30;

FIGS. 32 to 34, each, are a side view, in cross-section, showing a different modification showing a distal end portion of the apparatus above;

FIGS. 37 and 38, each, are a side view, in cross-section, showing a different modification of the above apparatus having a distal end portion of a probe.

DETAILED DESCRIPTION OF THE PREFERRED EMBODIMENTS

One embodiment of the present invention will be explained below with reference to FIGS. 1 to 5.

Figure 1:
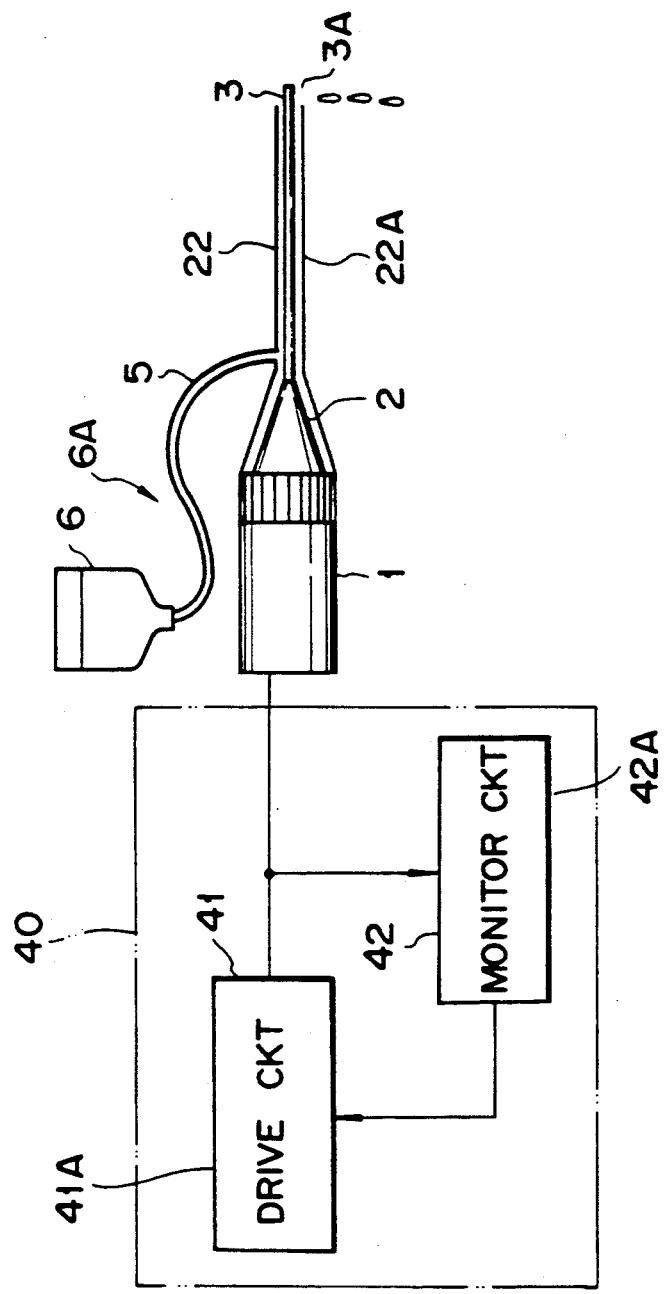
FIG. 1 is an overall view showing an ultrasound type treatment apparatus according to a first embodiment of the present invention.
Figure 2:
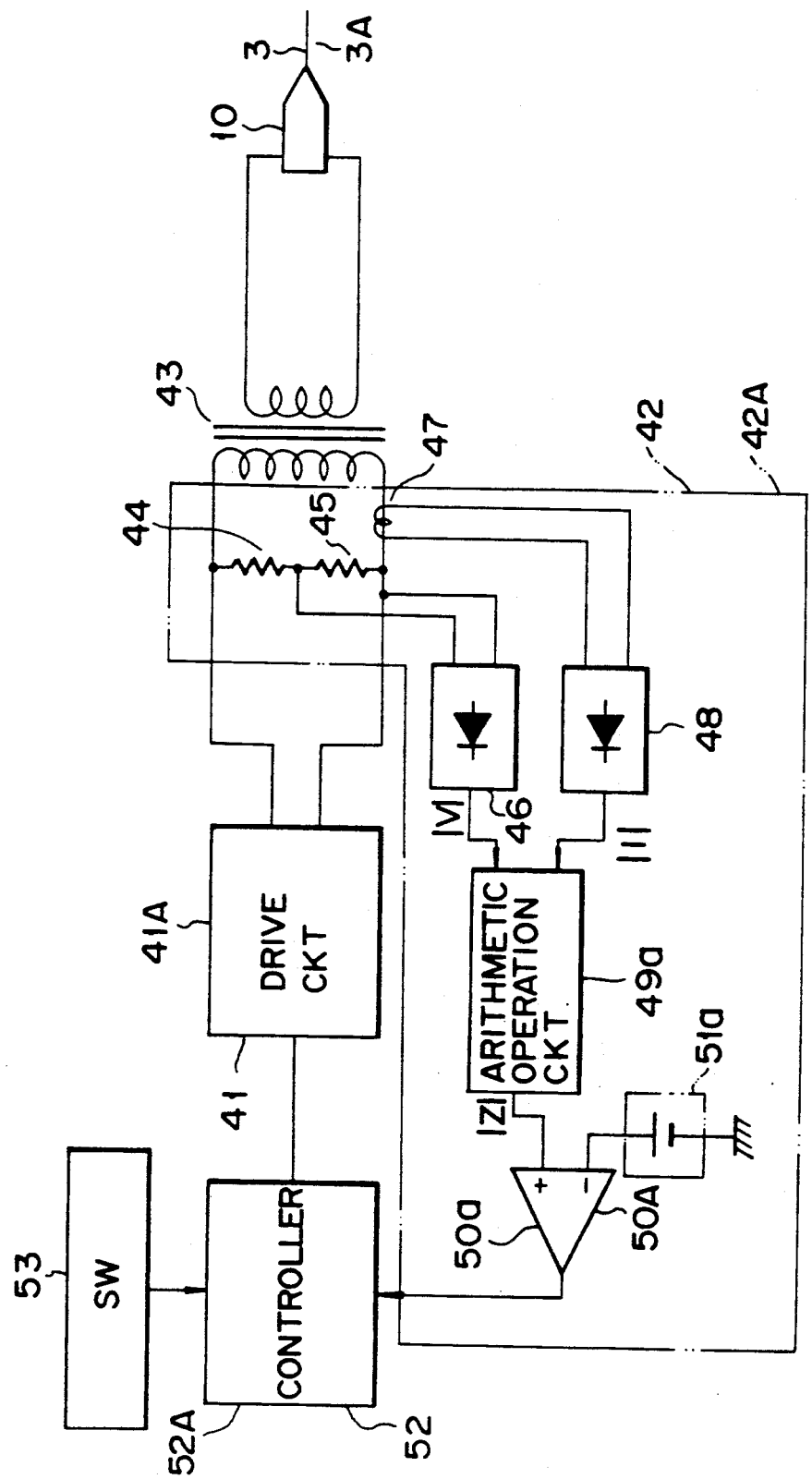
FIG. 2 is a view showing a practical electric circuit arrangement of the embodiment.

In FIG. 1, reference numeral 1 shows a handpiece for an ultrasound type treatment apparatus. An ultrasonic oscillation device 10 as shown in FIG. 2 is mounted in handpiece 1. A probe 3 at a location of an ultrasound transmitting means 3A is connected to the ultrasonic oscillation device 10 via a horn 2. This arrangement amplifies an ultrasonic oscillation wave of the ultrasonic oscillation device 10 at a location of the horn 2 and transmits it to the probe 3. The horn 2 and probe 3 are covered with a sheath 22 serving as a cooling water communication means as will be set forth below.

Figure 3:
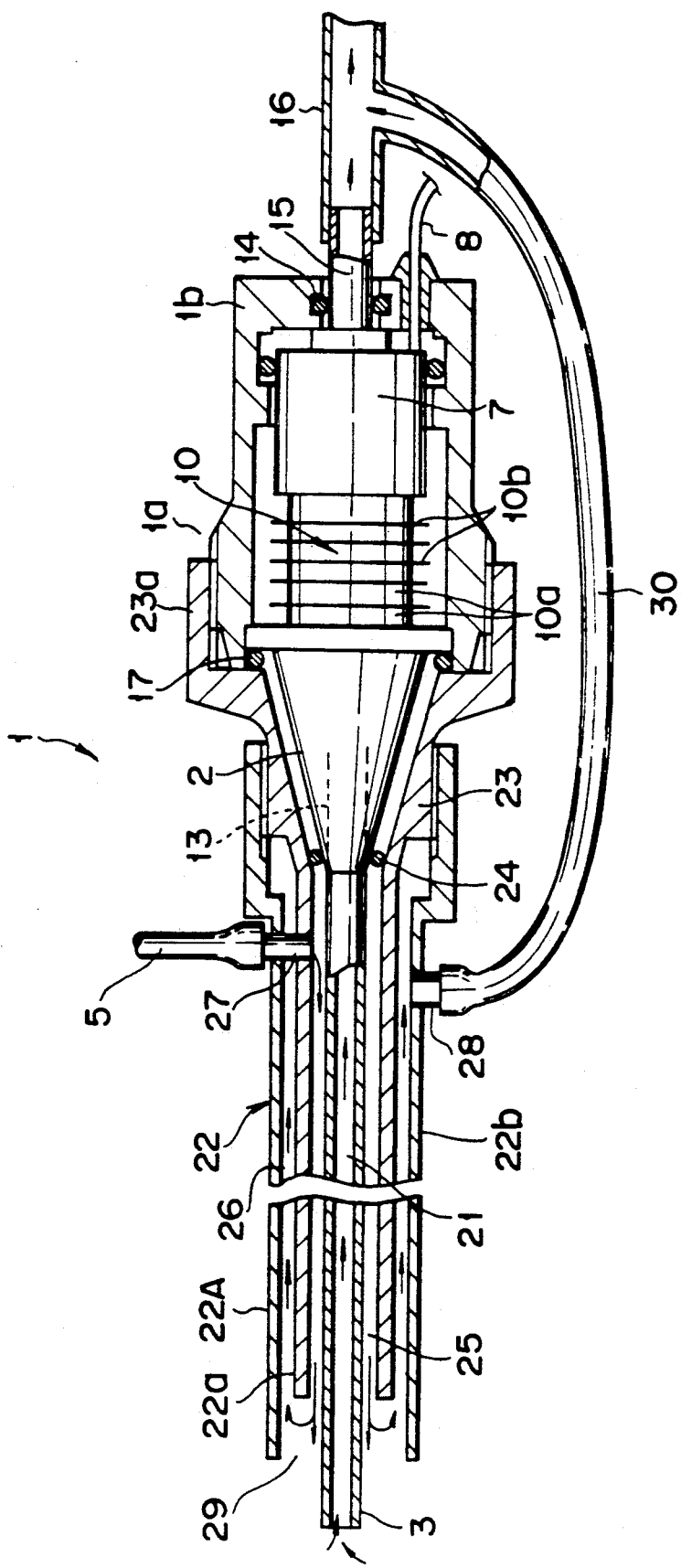
FIG. 3 is a side view, in cross-section, showing a detail of the ultrasound type treatment apparatus.

FIG. 3 shows a detailed internal structure of the handpiece 1. A cover 1b of a substantially bottomed-cylindrical configuration is provided at a grip section 1a of the handpiece 1 and the ultrasonic oscillation device 10 is mounted within the cover 1b.

The ultrasonic oscillation device 10 is composed of a laminated structure of piezoelectric elements (for example PZT) 10a and electrodes 10b. The horn 2 for amplifying the amplitude of the ultrasonic wave is connected to the forward end of the ultrasonic oscillation device 10. A back-up plate 7 is connected to the rear end of the ultrasonic oscillation device 10. Between the horn 2 and the back-up plate 7 the ultrasonic oscillation device 10 is fastened by a combination of a bolt, not shown, penetrating the back-up plate 7 and ultrasonic oscillation device 10 and an associated threaded nut to provide an integral structure. A power supply cord 8 is connected to the electrode 6 of the ultrasonic oscillation device 10.

A suction hole 13 is formed in the center of the horn 2 and in the bolt extending through the ultrasonic oscillation device 10 and back-up plate 7 to provide an axial communication hole. The rear end of the suction hole 13 is connected to a first suction tube 16 via a suction connector 15 extending through the rear end wall (bottom wall) of the cover 1b. A fitting groove for an O ring 14 is formed relative to the through hole of the suction connector 15 fitted at the rear end wall of the cover 1b. The outer peripheral surface of the suction connector 15 is held, in a water-tight fashion, relative to the through hole of the cover 1b with the use of the O ring 14 fitted in the fitting groove of the suction hole 15.

The first suction tube 16 is connected to a suction pump, not shown. The peripheral portion of the horn 2 is held, in a water-tight fashion, by an 0 ring 17 which is fitted relative to the inner surface of the cover 1b of the grip section 1a. The ultrasonic oscillation device 10 is held by the O rings 14 and 17 within the cover 1b in a water-tight fashion.

The probe 3 for oscillation wave transmission is formed of a hollow metal pipe and detachably connected to the forward end of the horn 2. The hole of the probe 3 provides a first suction hole or passage 21 for communicating with the suction hole 13.

The sheath 22 for covering the probe 3 and outer peripheral portion of the horn 2 is provided at the forward end portion of the handpiece 1. The sheath 22 is formed of a double tube having an inner tubular sheath section 22a and outer tubular sheath section 22b. A cover section 23 for covering the outer peripheral portion of the horn 2 is provided integral with the proximal end portion of the inner sheath section 22a. The cover section 23 has an inner taper surface corresponding to an outer peripheral surface of the horn 2. A cylindrical section 23a is formed integral with the proximal end portion of the cover section 23. An internally threaded section is provided on the inner wall portion of the sheath section 22a to engage with an externally threaded section provided on the outer peripheral surface of the forward end portion of the cover 1b of the grip section 1a. The cover section 23 is detachably threaded over the externally threaded portion of the cover 1b of the grip section 1a. An O ring 24 is provided between the inner surface of the forward portion of the cover section 23 and the outer peripheral surface of the forward end portion of the horn 2 to achieve a water-tight seal between the two.

An internally threaded portion is provided on the proximal end portion of the external sheath section 22b so as to be detachably threaded over the externally threaded portion of the outer peripheral surface portion of the cover section 23 of the inner sheath section 22a.

The inner sheath section 22a is concentrically inserted over the probe 3 to provide a spacing. The outer sheath section 22b is similarly inserted over the inner sheath section 22a to provide a concentric array of the probe, inner sheath section 22a and outer sheath section 22b. In this case, a spacing is provided between the outer sheath section 22b and the inner sheath section 22a, and between the inner sheath section 22a and the probe 3. A water supply passage 25 is provided, as a first passage, at the spacing between the probe 3 and the inner sheath section 22a. A suction passage 26 is provided, as a second passage 26, at the spacing between the inner sheath section 22a and the outer sheath section 22b.

A water supply connector 27 and second suction connector 28 are provided near the proximal end of the sheath 22 to communicate with the water supply passage 25 and suction passage 26, respectively. One end of a water supply tube 5 as shown in FIG. 1 is connected to the outer end of the water supply connector 27. The other end of the water supply tube 5 is connected to a cooling water tank (a water supply source) 6. A known water supply pump, not shown, is mounted on the cooling water tank 6. The cooling water tank 6, water supply pump and water supply tube 5 provide a cooling water means 6A by which the cooling water is supplied to the water supply passage 25 for the sheath 22.

One end of the suction tube 30 is connected to the suction connector 28 and the other end of the suction tube 30 is connected partway to the suction tube 16.

The inner sheath section 22a is so formed as to be shorter in length than the outer sheath section 22b with the distal end of the outer sheath section 22b extending farther than that of the inner sheath section 22a. A communication passage 29 is so provided at the distal end portion of the outer sheath section as to allow the water supply passage 25 to communicate with the suction passage 26.

The handpiece 1 is connected to a body 40 of the ultrasound type treatment apparatus.

The apparatus includes a drive circuit 41 serving as a drive means 41A for driving the ultrasonic oscillation device and a monitor circuit 42 serving as a monitor means 42A for monitoring the state of the ultrasonic oscillation device 10.

FIG. 2 shows a major section of a control circuit in the apparatus body 40.

The drive circuit 41 generates a drive signal and is connected to a primary coil of an output transformer 43. The ultrasonic oscillation element 10 is connected to a secondary coil of the output transformer 43. An ultrasound drive signal is delivered from the drive circuit 41 via the output transformer 43 to the ultrasonic oscillation device 10 in the handpiece 1.

A series circuit of resistors 44, 45 is connected in parallel with the primary coil of the output transformer 43. A rectifying circuit 46 is connected to the resistor 45 and a voltage across the resistor 45 is rectified at the rectifying circuit 46. The output voltage of the rectifying circuit 46 corresponds to an impression voltage V of the ultrasonic oscillation device 10.

A current detector 47 is provided in a connection line connected between the drive circuit 41 and the primary coil of the output transformer 43. A rectifying circuit 48 is connected to the current detector 47. An output voltage of the current detector 47 is rectified at the rectifying circuit 48. The output voltage of the rectifying circuit 48 corresponds to a current I flowing into the ultrasonic oscillation device 10.

The rectifying circuits 46 and 48 are connected to an arithmetic operation circuit 49a. Put it in another way, the output voltage of the rectifying circuit 46 (corresponding to a voltage applied to the ultrasonic oscillation device 10) and that of the rectifying circuit 48 (corresponding to a current I flowing into the ultrasonic oscillation device 10) are supplied to the arithmetic operation circuit 49a. Here the impedance Z of the ultrasonic oscillation device 10 is found by dividing an output voltage level of the rectifying circuit 46 by that of the rectifying circuit 48, that is V/I.

The arithmetic operation circuit 49a is connected to one (non-inverting input terminal (+)) of a non-inverting input terminal (+) and inverting input terminal (−) of a comparator 50a acting as a determining means 50A. An output voltage level of the arithmetic operation circuit 49a corresponding to an impedance Z is delivered to the non-inverting input terminal (+) of the comparator 50a.

A constant voltage circuit 51a serving as a reference value setting means is connected to the inverting input terminal (−) of the comparator 50a. Put it in another way, a predetermined voltage Vref of the constant voltage circuit is supplied to the inverting terminal (−) of the comparator 50a.

The output terminal of the comparator 50a is connected to a controller 52 serving as a control means 52A constituted by, for example, a microcomputer and associated peripherals. For example, the handpiece 1 or a start switch 53 and drive circuit 41, both mounted on the apparatus body 40, are connected to the controller 52. The output voltage of the comparator 50a is supplied to the controller 52. When the output voltage of the comparator 50a goes high, the controller 52 delivers a drive signal to the drive circuit 41 for drive. When the output voltage of the comparator 50a becomes a low level, the controller 52 stops the operation of the drive circuit 41.

A monitor circuit 42 is provided at a location from the resistor 44 toward the constant voltage circuit 51 and comprises an impedance detecting means for the monitor circuit 42 as a main section and a means for monitoring a drive state of the probe 3 and hence determining a water supply state and stopping a drive by the drive circuit 41 when there is any abnormal state.

The operation of the apparatus thus arranged will be explained below.

The sheath-covered probe 3 is inserted into a region of interest of a human body cavity with the grip section 1a of the handpiece 1 gripped by hand. Then a suction pump, not shown, is driven, applying a suction force to the first and second suction passages 21 and 26 via the first and second suction tubes 16 and 30.

The water supply pump, not shown, is driven, supplying water from the water supply tube 5 into the water supply passage 25 via the water supply connector 27 and then toward the distal end of the water supply passage 25. A greater quantity of water is fed into the body cavity of a human being, but some water is drawn via the communication passage 29 at the distal end portion of the sheath 22 back into the suction passage 26.

Figure 4:
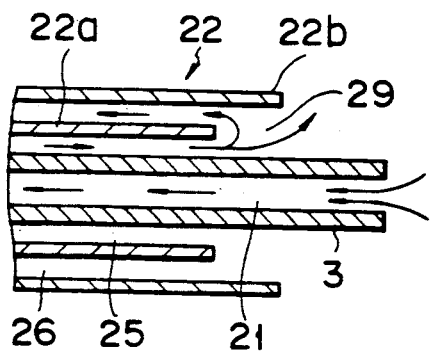
FIG. 4 is a side view, in cross-section, showing a distal end portion of a probe of the apparatus.

The water thus fed into the body cavity is sucked through the first suction passage 21 as shown in FIG. 4 after it has washed the body cavity clean. Any fragments of a tissue or a stone in the body cavity which are caused by the treatment of it by the probe, together with a perfused liquid, are drawn via the first suction passage 21 and also back into the first suction tube 16 through the suction hole 13.

The water sucked directly into the second suction passage 26 without being fed via the water supply passage 25 into the body cavity is supplied via the second suction tube 30, meets a stream flowing in the first suction tube 16, and is pumped back into a suction pump, not shown.

If the ultrasonic oscillation device 10 of the ultrasound type diagnostic apparatus is oscillated at a high output level and a resultant ultrasonic wave is transmitted by the probe 3, then the probe 3 is heated above a normal level. In order to prevent a temperature rise due to the generation of heat at the probe 3, a larger quantity of cooling water is flowed through the water supply passage 25. It is desirable at this time to strongly suck the water via the first suction tube 16.

If a larger quantity of water is flowed toward the body cavity of the human being, an increased quantity of water is drawn via the communication passage 29 back into the second suction passage 26 upon comparison with the water flow into the body cavity. As a result, a lesser quantity of water flows into the body cavity of the human being, thus preventing a flow of a larger quantity of water into the body cavity and a flush of the water there. It is thus possible to perform an efficient diagnostic treatment without the observation field being hindered.

Further, since the second suction passage 26 is provided in addition to the first suction passage 21, it is possible to prevent a suction force from being increased to any unnecessary extent via the first suction passage 21 even under a higher suction level. This arrangement can prevent the suction of the living tissue, etc., at the distal end of the probe 3. Since the first and second suction passages 21 and 26 meet at a proximal end side, if the first suction passage 21 is clogged, then an increased amount of suction is involved and hence it is possible to prevent a living tissue, for example, from being sucked to the distal end of the probe 3.

Figure 5:
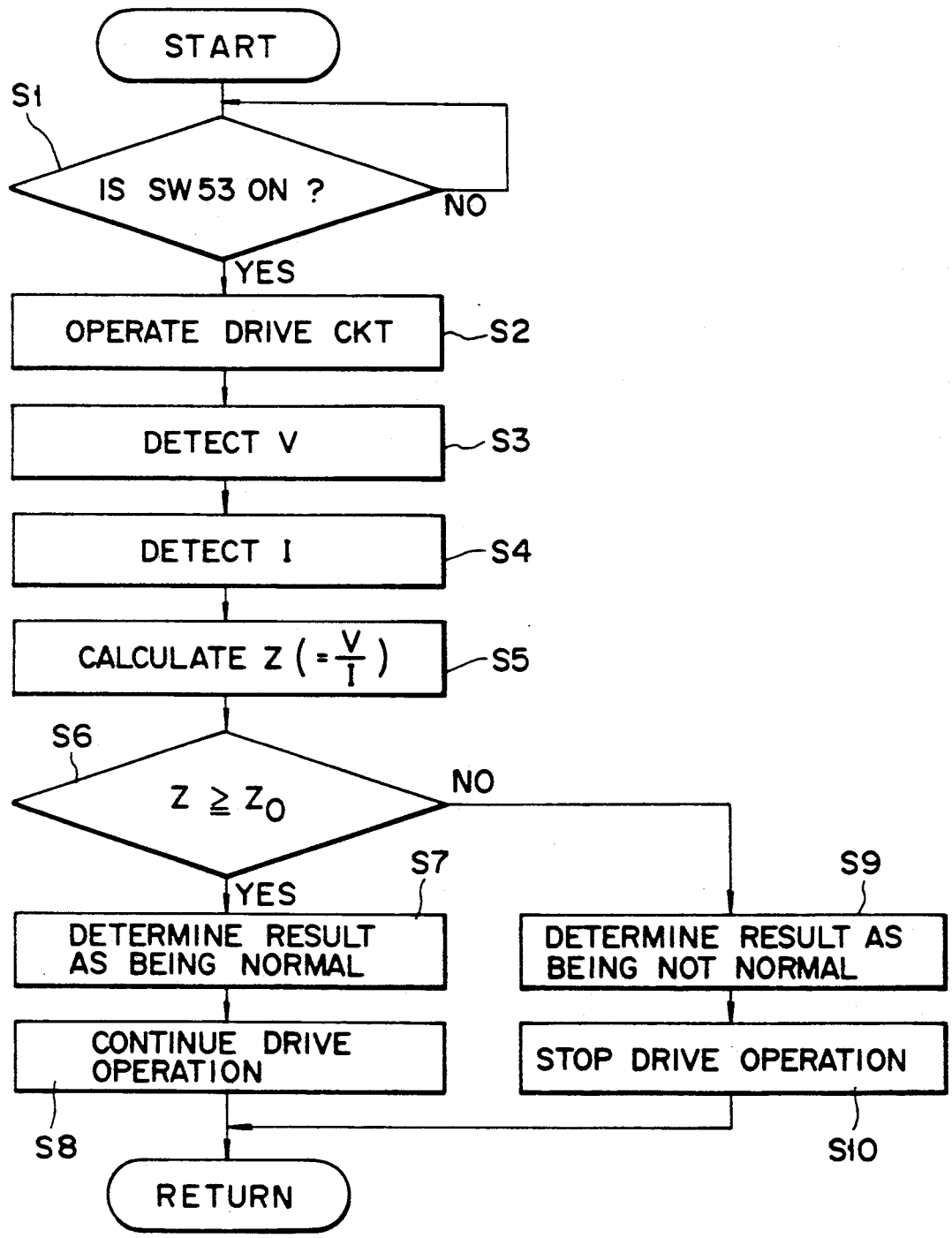
FIG. 5 shows a flowchart for explaining the operation of the embodiment of the present invention.

The operation of the controller 52 when the aforementioned diagnostic treatment is utilized will be explained below with reference to a flowchart shown in FIG. 5.

Step S1 detects an ON operation of the start switch 53 mounted on the handpiece 1 or the apparatus 40. At step S2, a drive signal is delivered from the controller 52 to the drive circuit 41 and the drive circuit 41 starts its start operation. The drive circuit 41, upon being driven, delivers a high frequency signal via the output transformer 43 to the ultrasonic oscillation device 10 in the handpiece 1. By so doing, the ultrasonic oscillation device 10 is driven to allow an ultrasonic oscillation wave to be transmitted to the probe 3. At that time, the probe 3 is oscillated in a longitudinal wave mode and distorted at the nodes of the longitudinal wave, so that the probe 3 tends to be raised in temperature. In this case, the cooling water held in the cooling water tank 6 is flowed into the sheath 22 via the water supply tube 5, preventing a temperature rise in the probe 3 and hence a fatigue and destruction in the probe 3.

During the operation of the drive circuit 41 a voltage normally developed across the resistor 45 is rectified at the rectifying circuit 46. The output voltage of the rectifying circuit 46 which corresponds to an application voltage V to the ultrasonic oscillation device 10 is input to the arithmetic operation circuit 49a—step S3. At the same time, the voltage created at the current detector 47 is rectified by the rectifying circuit 48 and the output voltage of the rectifying circuit 48 (corresponding to a current I flowing through the ultrasonic oscillation device 10) is input to the arithmetic operation circuit 49a—step S4. The arithmetic operation circuit 49a detects an impedance Z of the ultrasonic oscillation device 10 by dividing the output voltage level of the rectifier 46 by the output voltage level of the rectifier 48—step S5.

A voltage whose level corresponds to an impedance Z delivered from the arithmetic operation circuit 49a is supplied to the non-inverting input terminal (+) of the comparator 50a. A constant voltage (V ref) is supplied from the constant voltage circuit 51a to the inverting input terminal (−) of the comparator 50a. The comparator 50a compares a detection value of the impedance Z of the ultrasonic oscillation device 10 with a set value which is set by a predetermined voltage (V ref) supplied from the constant voltage circuit 51a— step S6. Here the output voltage of the comparator 50a goes high when the impedance Z as detected by the arithmetic operation circuit 49a is higher than the predetermined value $Z_0$. The aforementioned high impedance of the ultrasonic oscillation device 10 means that cooling water is being positively supplied to the probe 3. In this state, the controller 52 determines that the level is normal (step S7), continuing the operation of the drive circuit 41 (step S8).

If, on the other hand, the impedance Z as detected by the arithmetic operation circuit 49a is smaller than the predetermined value $Z_0$, the output voltage of the comparator 50a becomes a low level, meaning that the cooling water tank 6 becomes empty or the cooling water fails to be supplied to the probe 3, that is, the impedance Z becomes an extremely low level due to the ultrasonic oscillation element 10 placed in a non-loaded state. The controller 52 determines that this state is abnormal—step S9. The controller 52 stops the operation of the drive circuit 41 as an abnormal stop mode—step S10. It is thus possible to previously prevent a temperature rise in the probe 3 and hence a fatigue or destruction in the probe 3.

Figure 7:
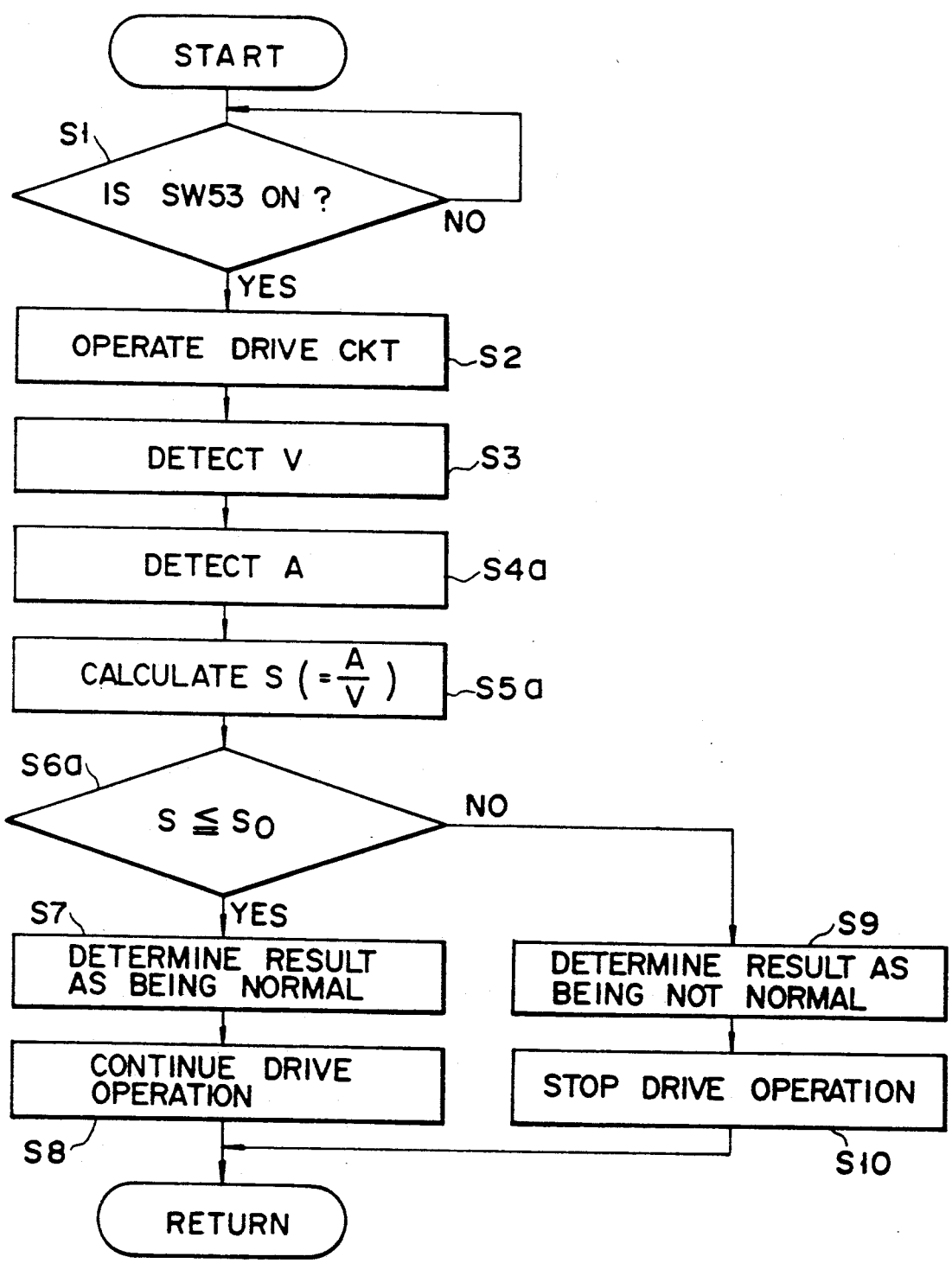
FIG. 7 shows a flowchart for explaining the operation of the embodiment above.

A second embodiment of the present invention will be explained below with reference to FIGS. 6 and 7.

In the second embodiment, an oscillation pickup 61 and oscillation detector 62 are employed in place of the current detector 47 and rectifier 48 in a monitor circuit 42 of the first embodiment.

The oscillation pickup 61 is mounted on the ultrasonic oscillation device 10 in the second embodiment. The oscillation detector 62 delivers a voltage whose level corresponds to an oscillation amplitude A of the ultrasonic oscillation device 10 as detected by the oscillation pickup 61, that is, the oscillation detector 62 delivers such an output signal to an arithmetic operation circuit 49b and an output voltage of the rectifier 46 is also delivered to the arithmetic operation circuit 49b. The arithmetic operation circuit 49b divides an output voltage level of the oscillation detector 62 by an output voltage level of the rectifier 46, that is, performs a division of A/V.

The arithmetic operation circuit 49b delivers an output voltage corresponding to a calculation value S (=A/V) to an inverting input terminal (−) of the comparator 50b and, at this time, a constant voltage (V ref) is supplied from a constant voltage circuit 51b be to a non-inverting input terminal (+) of the comparator 50b.

The other arrangement of the second embodiment is the same as that of the first embodiment The operation of the second embodiment will be explained below with reference to a flowchart of FIG. 7.

Upon the driving of the ultrasonic oscillation device 10, an oscillation amplitude A of the ultrasonic oscillation device 10 is supplied to the oscillation pickup 61 and oscillation detector 62 for detection — S4a. Here, the oscillation amplitude A of the ultrasonic oscillation device 10 becomes greater when no cooling water is supplied to the probe 3 than when cooling water is positively supplied to the probe 3.

When the cooling water is positively supplied to the probe 3, an output voltage of the comparator 50b goes high at step S6a since at step S5a a calculation value S ($=A/V$) of the arithmetic operation circuit 49b is made lower than a predetermined value $S_0$. In this case, a controller 52 determines that state as being normal (step S7) and the operation of the drive circuit 41 is continued (step S8).

If the cooling water tank 6 becomes empty or no cooling water is supplied to the probe 3 due to the detachment of the water supply tube 5 from an associated member, a calculation value S of the arithmetic operation circuit 49b is made higher than the predetermined value $S_0$ (step S5a). In this case, the controller 52 determines that state as being abnormal at step S9 and the operation of the drive circuit 41 is stopped—Step S10.

It is thus possible to previously prevent a temperature rise in the probe 3 and hence a fatigue and destruction in the probe 3.

Figure 8:
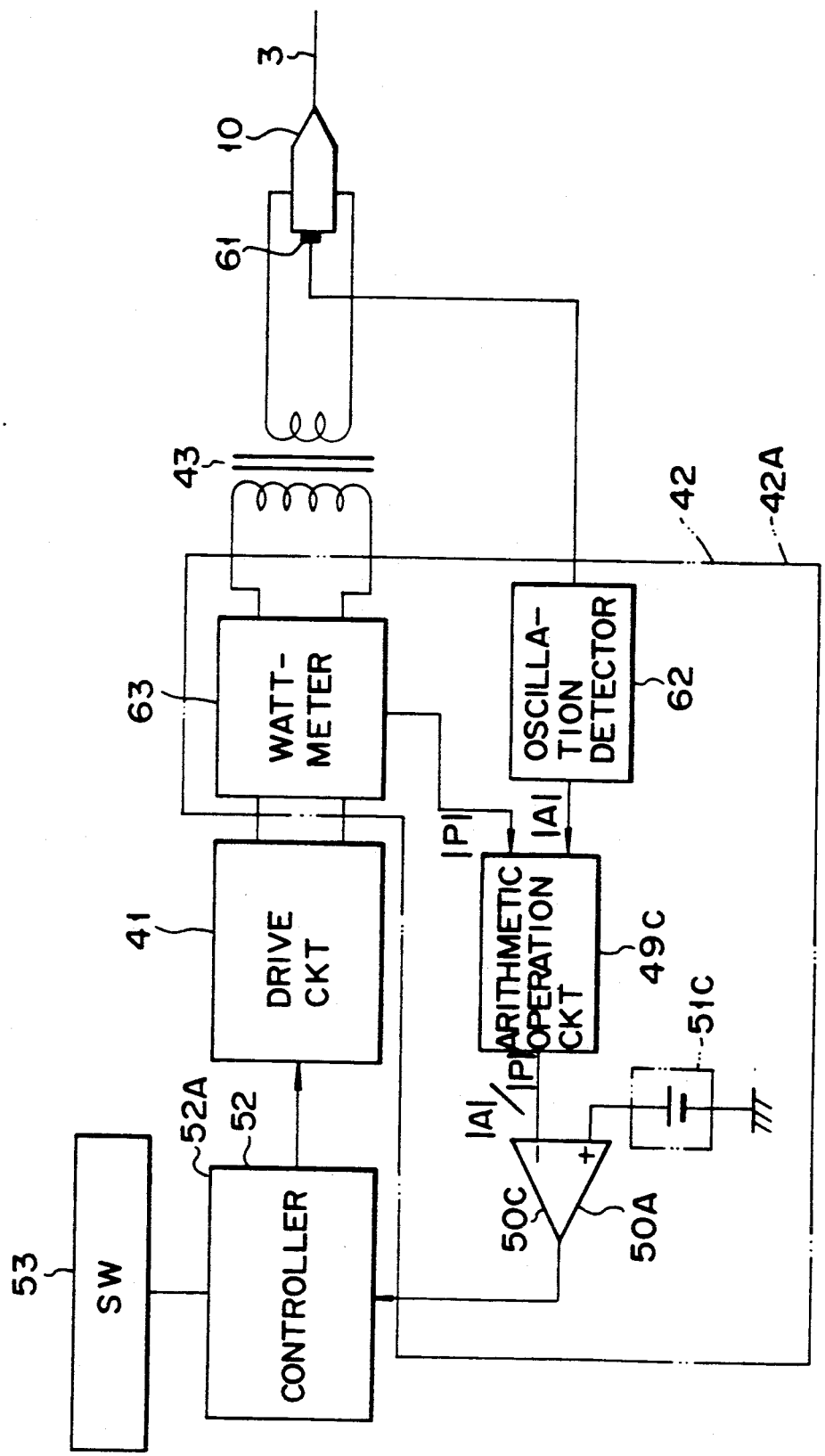
FIG. 8 is a schematic view showing a major section of an ultrasound type treatment apparatus according to a third embodiment of the present invention.
Figure 9:
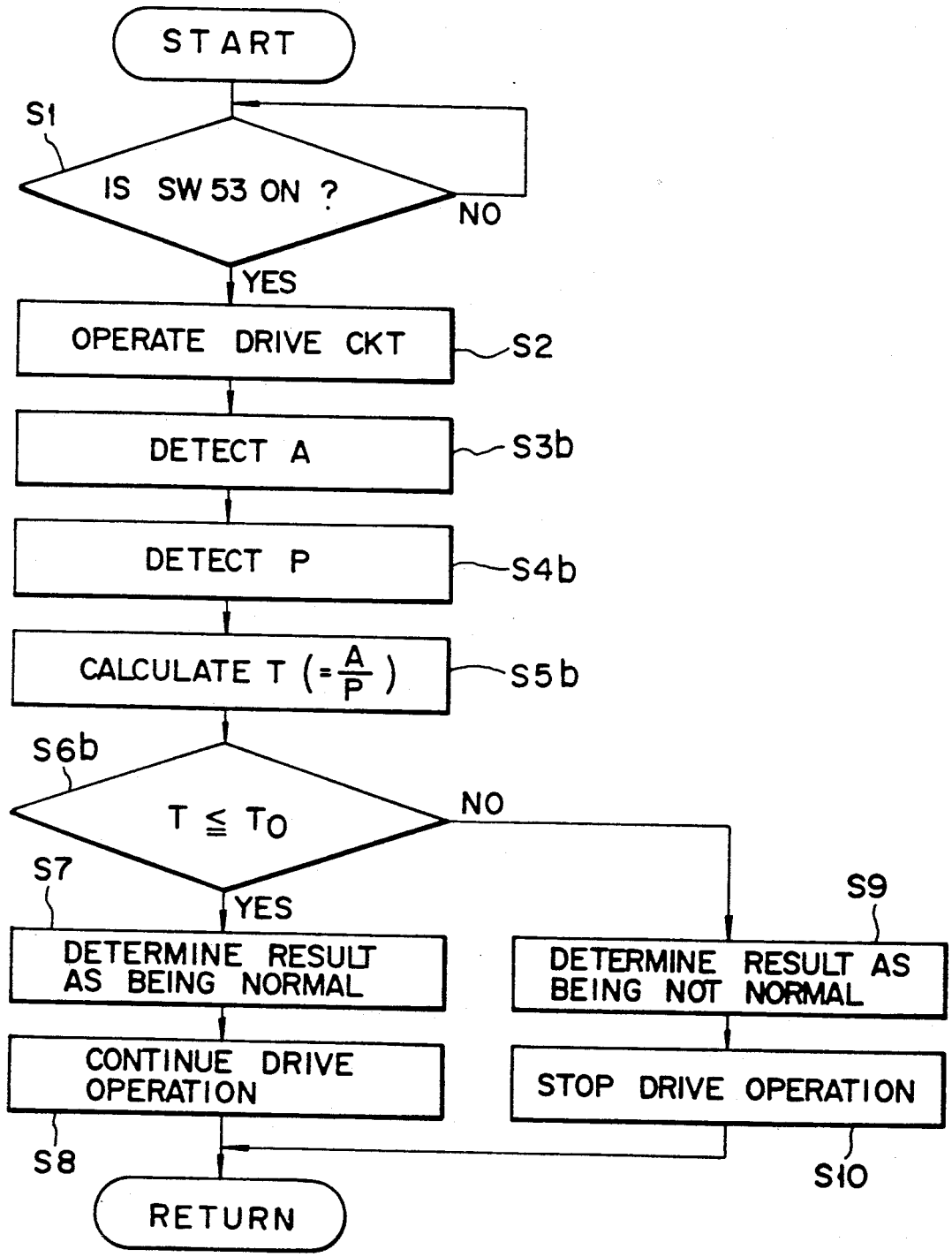
FIG. 9 shows a flowchart for explaining the function of the embodiment of FIG. 8.

FIGS. 8 and 9 show a third embodiment of the present invention.

The third embodiment employs a wattmeter 63 in place of resistors 44 and 45 and rectifier 46 in the monitor circuit 42 in the second embodiment.

The wattmeter 63 detects a dissipation power P in the ultrasonic oscillation device 10 and delivers a corresponding voltage to an arithmetic operation circuit 49c and an output voltage of an oscillation detector 62 is supplied to the arithmetic operation circuit 49c. The arithmetic operation circuit 49c divides an output voltage level of the oscillation detector 62 by that of the wattmeter 63, that is, performs a division (A/P) operation.

The arithmetic operation circuit 49 delivers a voltage whose level corresponds to a calculation value T ($=A/P$).

The other arrangement of the third embodiment is the same as that of the second embodiment.

The operation of the third embodiment will be explained below with reference to a flowchart of FIG. 9.

Upon the driving of the ultrasonic oscillation device 10, an oscillation amplitude A of the ultrasonic oscillation device 10 is supplied to an oscillation pickup 61 and oscillation detector 62 for detection— step S3b. A power dissipation P of the ultrasonic oscillation device 10 is detected by the wattmeter 63— step S4b.

The dissipation power P is made lower when no cooling water is supplied to the probe 3 than when cooling water is positively supplied to the probe 3.

When the cooling water is positively supplied to the probe 3, a calculation value T ($=A/P$) of the arithmetic operation circuit 49c is made smaller than a predetermined value $T_0$ (step S5b) and an output voltage of the comparator 50c goes high at step S6b. A controller 52 determines that state as being normal (step S7) and a drive circuit 41 continues its operation (step S8).

If the cooling tank 6 becomes empty or no cooling water is supplied to the probe 3 due to the detachment of the water supply tube 5 from the associated member, the calculation value T ($=A/P$) of the arithmetic operation circuit 49 is made greater than a predetermined value $T_0$ and the output voltage of the comparator 50c becomes a low level. In this case, the controller 52 determined that state as being abnormal (step S9) and the drive circuit 41 stops its operation (step S10).

It is possible to previously prevent a temperature rise in the probe 3 and hence a fatigue and destruction in the probe.

Figure 11:
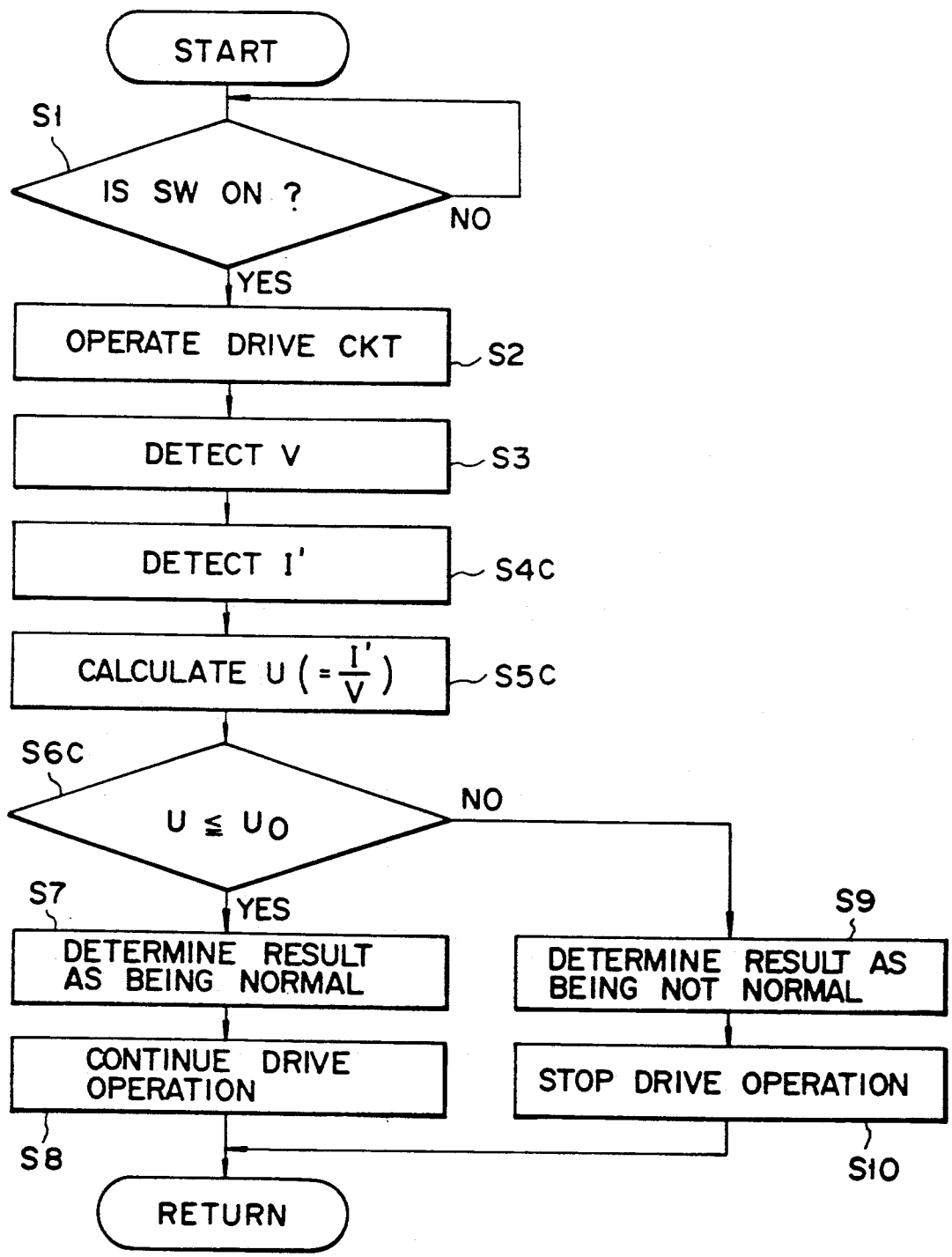
FIG. 11 shows a flowchart for explaining the function of the fourth embodiment.

FIGS. 10 and 11 show a fourth embodiment of the present invention.

Generally, an electrostrictive oscillation device, such as the ultrasonic oscillation device 10, reveals a substantially proportional relation between the drive current and the oscillation amplitude A. Here, a constant current drive is employed so as to obtain a predetermined oscillation amplitude A of the ultrasonic oscillation device 10.

In the fourth embodiment of the present invention, a constant current power source circuit 72 is connected to an alternating current source 71 and to a drive circuit 41 in which case the constant current power source circuit 72 serves as an operation power source for a drive circuit 41.

A current detection 73 is used in place of the current detector 47 and rectifier 48 in the monitor circuit 42 in the first embodiment. The current detector 73 is provided in a connection line between the constant current source circuit 72 and the drive circuit 41.

Here, the output voltage of the current detector 73 corresponding to a constant current I' is supplied to an arithmetic operation circuit 49d and an output voltage of a rectifier 46 is supplied to the arithmetic operation circuit 49d. The arithmetic operation circuit 49d divides an output voltage level of the current detector 73 by an output voltage level of the rectifier 46, that is, performs a division ($I'/V$) operation.

The arithmetic operation circuit 49d delivers a voltage corresponding to a calculation value U ($=I'/V$) to a inverting input terminal ($-$) of a comparator 49d.

A constant voltage circuit 51d supplies a constant voltage (V ref) to a non-inverting input terminal ($+$) of the comparator 50d.

The other arrangement of the fourth embodiment is the same as that of the first embodiment.

The operation of the fourth embodiment will be explained below with reference to a flowchart of FIG. 11.

Upon the driving of an ultrasonic oscillation device 10, its oscillation amplitude is held in a constant state by a constant current output of the constant current source circuit 72.

A voltage V which is applied to the ultrasonic oscillation device 10 is smaller than when no cooling water is supplied to a probe 3 than when cooling water is positively supplied to the probe 3.

When the cooling water is positively supplied to the probe 3, a calculation value U ($=I'/V$) of the arithmetic circuit 49d is made lower than a predetermined value $U_0$ at step S5c and an output voltage of the comparator 50d becomes a high level (step S6c). The controller 52 determines this state as being normal (step S7) and the drive circuit 41 continues its operation (step S8).

If the cooling water tank 6 becomes empty or cooling water fails to be supplied to the probe 3 due to the detachment of the water supply tube 5 from the associated member, a calculation value U ($=I'/V$) of the arithmetic operation circuit 49d is made higher than a predetermined value UO (at step S5c) and the output voltage of the comparator 50d becomes a low level (step S9). The drive circuit 41 stops its operation (step S10).

It is thus possible to previously prevent a temperature rise in the probe 3 and hence a fatigue and destruction in the probe 3.

Figure 12:
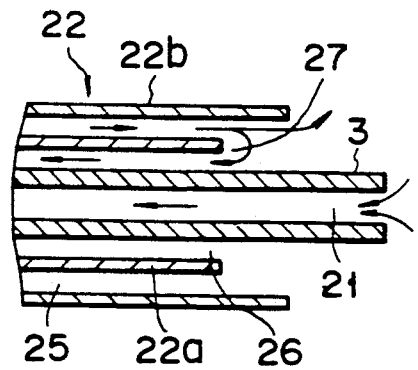
FIG. 12 is a side view, in cross-section, showing a distal end portion of a probe in a fifth embodiment of the present invention.

FIG. 12 shows a fifth embodiment of the present invention. In the fifth embodiment, a sheath 22 for covering a probe 3 is composed of inner and outer sheath sections 22a and 22b with a water supply passage 25 provided in a spacing between the inner sheath section 22a and the outer sheath section 22b. A second suction passage 26 is provided in a spacing between the inner sheath section 22a and the probe 3. The forward end of the inner sheath section 22a is shorter in length than that of the outer sheath section 22b to provide a communication passage 27. Except for this feature, the fifth embodiment is the same as the first embodiment.

Even in this embodiment, some of water which is supplied via the water supply passage 25 can be sucked directly from the second suction passage 26 without being supplied into a body cavity of a human being. If more water is to be supplied in order to enhance a cooling effect upon the probe 3, more water is drawn directly through the second water supply passage 26, without being sent into the body cavity, so that less water is sent into the body cavity. This prevents an accumulation of too much water in the body cavity or flushing of water there and hence prevents a restricted observation field and a subsequent lowered treatment operation.

Figure 13:
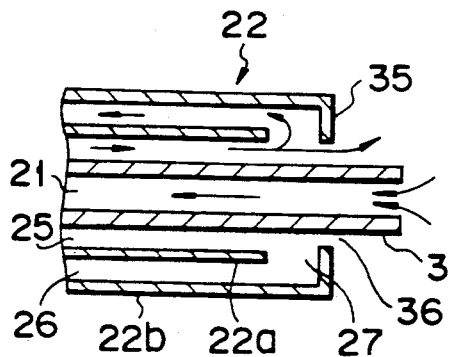
FIG. 13 is a side view, in cross-section, showing a distal end portion of a probe in a sixth embodiment of the present invention.

FIG. 13 shows a sixth embodiment of the present invention. In this embodiment, an inwardly projecting cover flange 35 is provided at the sheath 22 of the first embodiment such that it is located at the distal end of an outer sheath section 22b extending to a longer extent than that of the inner sheath section 22a. A gap 36 is provided between the cover flange 35 and the outer periphery of the probe 3, facilitating the ease with which water is drawn from the water supply passage 25 into a second suction passage 26 which is provided as a spacing between the inner sheath section 22a and the outer sheath section 22b. The other arrangement of the sixth embodiment is the same as that of the first embodiment.

Figure 14:
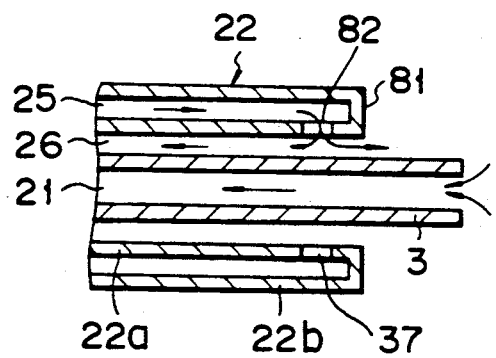
FIG. 14 is a side view, in cross-section, showing a distal, end portion of a probe in an ultrasound type treatment apparatus according to a seventh embodiment of the present invention.

FIG. 14 shows a seventh embodiment of the present invention. In this embodiment, an end plate 81 is provided in the sheath 22 of the fifth embodiment (FIG. 12) such that it blocks a gap between the distal end of the inner sheath section 22a and that of the outer sheath section 22b. A plurality of water supply holes 82 are provided as passages to allow water to flow from a water supply passage 25 into a second suction passage 26 provided as a spacing between the inner sheath section 22a and the probe 3. This arrangement can facilitate ready suction of water from the water supply passage 25 into the second suction passage 26. The other arrangement is the same as that of the fifth embodiment of the present invention.

Figure 15:
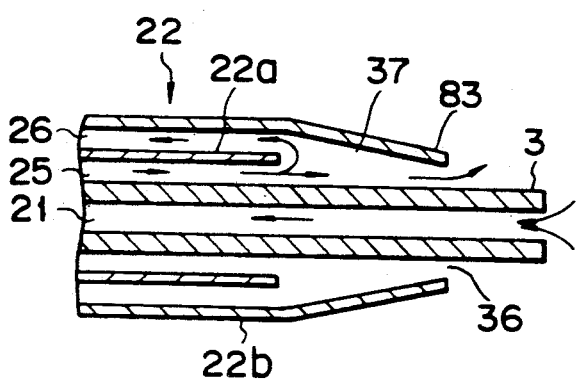
FIG. 15 is a side view, in cross-section, showing a distal end portion of a probe in an eighth embodiment of the present invention.

FIG. 15 shows an eighth embodiment of the present invention. In this embodiment, an inwardly directing taper cover section 83 is provided in place of the cover flange of the sheath 22 of the sixth embodiment (FIG. 13). A water supply gap 36 is provided between the taper cover section 83 and the outer periphery of a probe 3. Put it in another way, a second suction passage 26 is provided, without largely opening the distal end of the sheath 22, so that a suction function is facilitated in a supply of water from a water supply passage 25, into a second suction passage 26 which is defined between the inner sheath section 22a and the outer sheath section 22b. Further, since the distal end portion of the sheath 22 is tapered relative to the probe 3, it is possible to readily observe a treating end of the probe 3 in a region of interest of the human being. The other arrangement of the present invention is the same as that of the sixth embodiment of the present invention.

Figure 16:
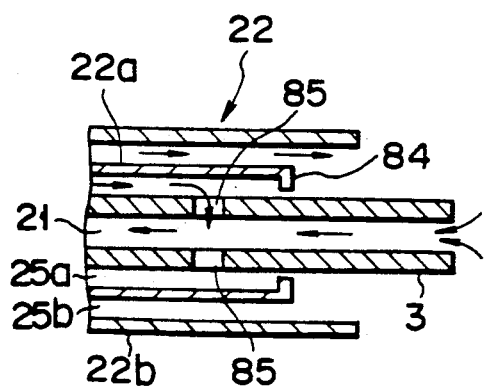
FIG. 16 is a side view, in cross-section, showing a distal end portion in the ultrasound type diagnostic apparatus.

FIG. 16 shows a modified form of a distal end portion of a probe for an ultrasound type treatment apparatus. In this modification, a water supply passage 25a is provided between an inner sheath section 22a of a sheath 22 and the outer periphery of the probe 3 and a water supply passage 25b between the inner sheath section 22a and an outer sheath section 22b. The distal end of the inner water supply passage 25a is substantially blocked by a cover flange 84 formed on the distal end of the inner sheath section 22a and projecting toward a probe 3. A plurality of communication holes 85 are formed in the distal end portion of the probe 3 to allow a suction passage 21 of the probe 3 to communicate with the inner water supply passage 25a. Since a water stream flowing through the inner water supply passage 25a is directly drawn by the communication holes 85 into the suction passage 21, it can be prevented from being flowed into a body cavity of a human being. For this reason, more water is supplied through the inner water supply passage 25a, ensuring an added cooling effect and at the same time preventing an added flow of water from the sheath into the body cavity.

Figure 17:
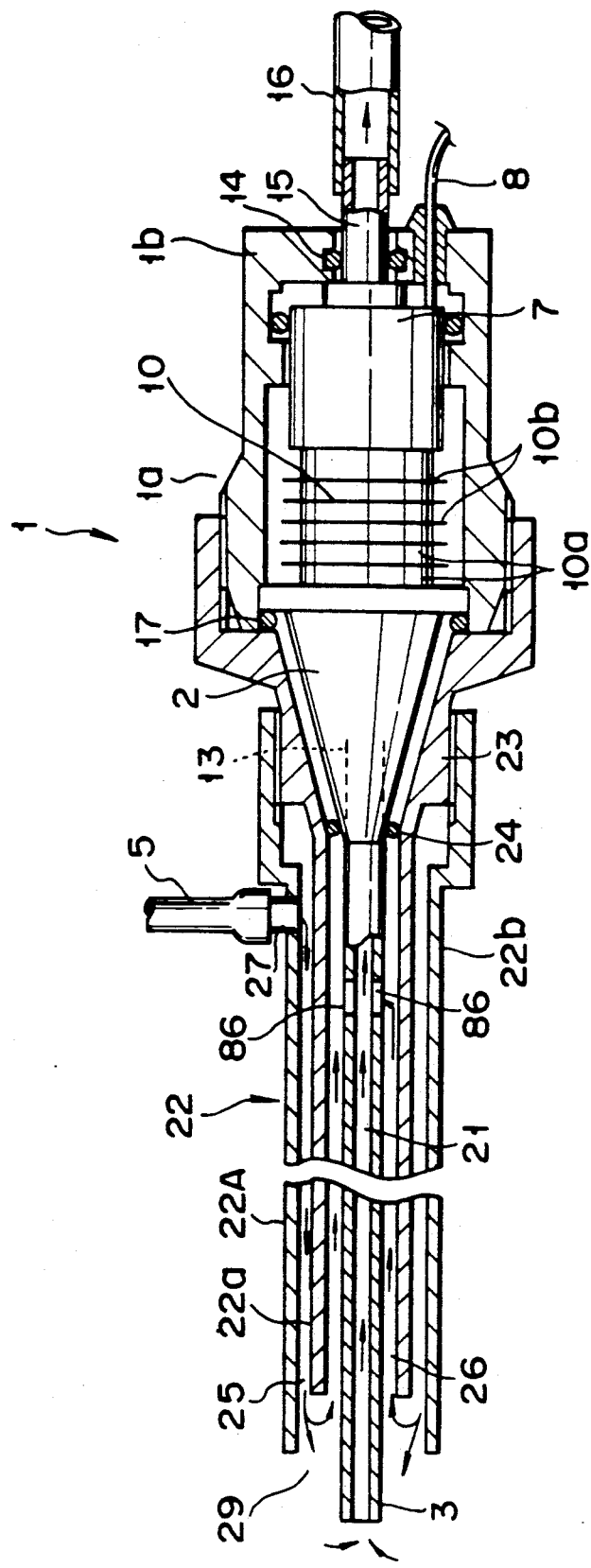
FIG. 17 is a side view, in cross-section, showing a ninth embodiment of the present invention.

FIG. 17 shows a ninth embodiment of the present invention. In the ninth embodiment, a plurality of suction holes 86 are provided in the proximal end portion of the probe 3 in the arrangement of the fifth embodiment (FIG. 12) to allow a first suction passage 21 in the probe 3 to communicate with a second suction passage defined between the outer periphery of the probe 3 and an inner sheath section 22a of a sheath 22.

This arrangement can obviate the need of providing a second suction connector 28 for a dedicated purpose and second suction tube 32 which are connected to the second suction passage 26. It is thus possible to obtain compact treatment apparatus of a simple structure.

Figure 18:
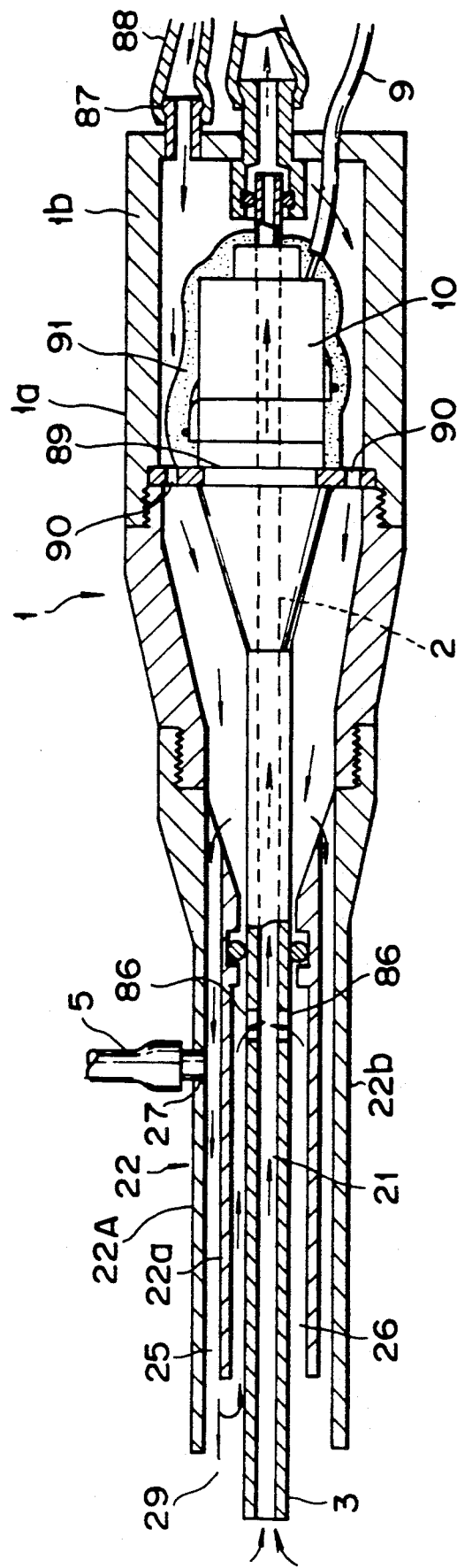
FIG. 18 is a side view, in cross-section, showing an ultrasound type treatment apparatus according to a tenth embodiment of the present invention.

FIG. 18 shows a tenth embodiment of the present embodiment. In this embodiment, some water is supplied via the inside of a cover 1b of a grip section 1a of a handpiece 1 into a water supply passage 25 in the arrangement of the ninth embodiment (FIG. 17). A second water supply connector 87 is fitted into the rear end wall of the cover 1b and a second water supply tube 88 is connected to the second water supply connector 87. A plurality of communication holes 90 are provided in a flange 89 of a horn 2 for water supply. The inside of the cover 1b of the grip section 1a communicates with the water supply passage 25 of a sheath 22. It is to be noted that a water-tight material 91 is covered around an ultrasonic oscillation device 10.

In the arrangement as set out above, the water can be supplied into the inside of the grip section 1a of the handpiece 1 via the second water supply tube 88 and second water supply connector 87 to allow the ultrasonic oscillation device 10 in the cover 1b to be cooled. Further, water can be supplied via the inside of the grip section 1a of the handpiece 1, allowing the probe 3 to be cooled with more water.

Figure 19:
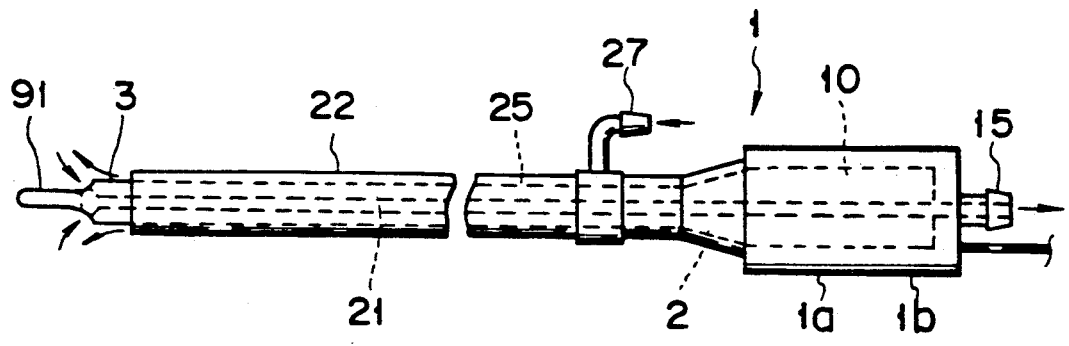
FIG. 19 is a side view showing the major section of an ultrasound type treatment apparatus according to an eleventh embodiment of the present invention.
Figure 20:
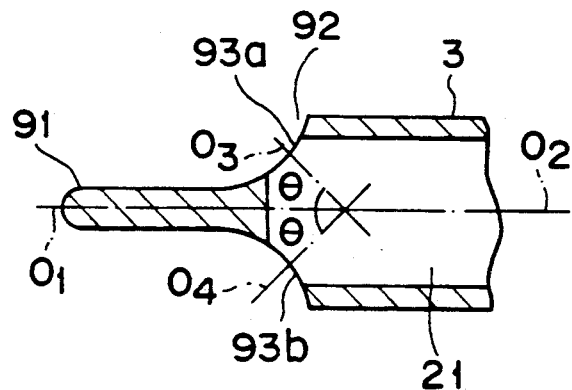
FIG. 20 is a side view, in cross-section, showing a major section of the embodiment.
Figure 21:
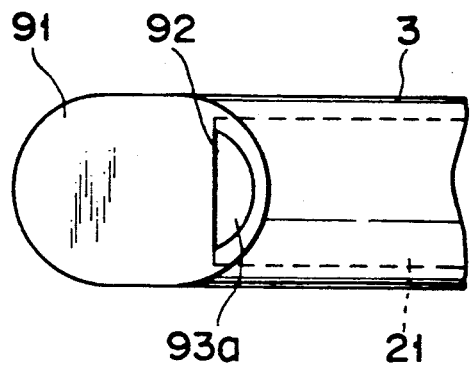
FIG. 21 is an enlarged view the embodiment.

FIGS. 19 to 21 show an eleventh embodiment of the present invention.

A substantially flat-like projection 91 is provided integral with the distal end of a probe 3 of a handpiece 1 (FIG. 19) so as to separate a united tissue or remove a mucous tissue of a human being. In the arrangement shown in FIG. 20, the flat-like projection 91 has a center axis $O_1$ which aligns with a center axis $O_2$ of the probe 3. The projection 91 is made thicker at the base end than at the distal end, that is, is continuously increased in thickness partway of its axial length toward the base end.

A pair of openings 93a, 93b are provided at a boundary area between the projection 91 and the probe 3, that is, at both the sides of the projection 91, to allow these openings to communicate with a suction passage 21. Here, the openings 93a and 93b have their center axes $O_3$ and $O_4$ diagonally extending relative to the center axis $O_2$ of the probe 3, that is, their center axes $O_3$ and $O_4$ intersected with respect to each other at a predetermined set angle 8 on the center axis $O_2$ of the prove 3.

At the time of diagnostic treatment, the distal end of the projection 91 which is provided on the distal end of the probe 3 can be brought into contact with an affected tissue of a human being and can separate a united tissue or remove a mucous tissue by applying an ultrasonic oscillation to the tissue. At this time, cooling water, while cooling the probe 3 raised in temperature by the ultrasonic oscillation, is supplied through the water supply passage 25 of the sheath 22 into the body cavity and is drawn, together with fragments of emulsified or resected tissue and body fluid, back into an outside via the suction passage 21.

In this arrangement, since the projection 91 is made thicker at the base end than at the distal end, it is possible to provide a larger cross-sectional area at a joint between the projection 91 and the probe 3, and hence to reduce a transmission loss of ultrasonic oscillation. Further, the projection 91 ensures a firmer and more durable structure. It is also possible to provide the ultrasonic oscillation device 10 with a relatively large amplitude and hence to further enhance a treatment efficiency of treatment.

The handpiece 1 can be driven with high efficiency since as many echoes of ultrasonic oscillation as possible can be reduced at the distal end of the probe 3. A high operability can also be gained due to the thinner distal end portion of the probe 3. As the openings 93a and 93b are provided with their center axes 93a and 93b diagonally intersected on the center axis $O_2$ of the probe 3, the opening areas of the openings 93a and 93b can be made larger than when the openings 93a and 93b are so formed at both sides of the projection 91 as to be in parallel with the center axis of the projection 91. It is thus possible to prevent the fragments of a resected tissue from being caught at the openings 93a and 93b.

Figure 22:
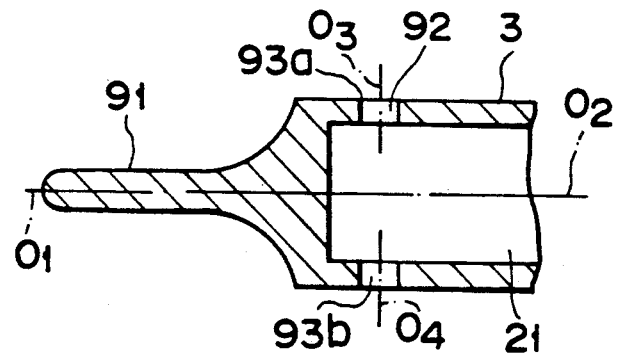
FIG. 22 is an enlarged view, in cross-section, showing a twelfth embodiment of the present invention.

FIG. 22 shows a twelfth embodiment of the present invention.

In this embodiment, those openings 93a and 93b at the projection 91 of the eleventh embodiment (FIGS. 19 to 21) are provided at the distal end portion of a probe 3 with their center axes $O_3$ and $O_4$ intersected at an angle perpendicular to the center axis $O_2$ of the probe 3. The other basic arrangement and function are the same as those of the eleventh embodiment.

Here, the number, position, shape, size etc. of the openings 93a and 93b can freely be selected irrespective of the shape of the projection 91. Further, the projection 91 can be rigidly secured to the probe 3 because no gap is left at a boundary between the projection 91 and the probe 3. It is also possible to provide a firm structure to the projection 91 with less transmission loss of ultrasonic oscillation.

Figure 23:
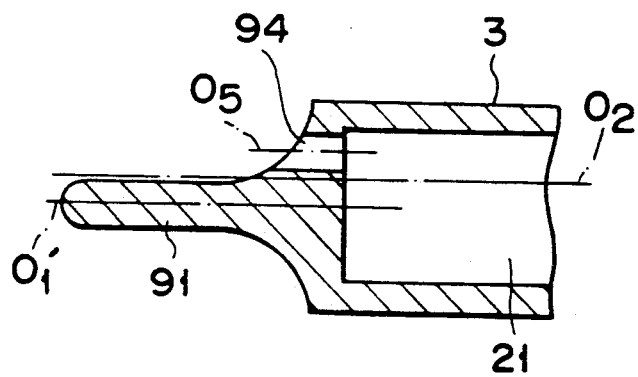
FIG. 23 is an enlarged view, in cross-section, showing a thirteenth embodiment of the present invention.

FIG. 23 shows a thirteenth embodiment of the present invention.

In this embodiment, the projection 91 at the eleventh embodiment (FIGS. 19 to 21) is provided parallel to a center axis $O_2$ of a probe 3 in an eccentric fashion with the center axis $O_1'$ of the projection 91 run parallel to the center axis $O_2$ of the probe 3. Further, an opening 94 is provided at a boundary between the projection 91 and the probe 3 to communicate with a suction passage 21 with the center axis $O_5$ of the opening 94 extending in parallel with that of the probe in an eccentric fashion. The other arrangement and function of the thirteenth embodiment are the same as those of the eleventh embodiment.

In the thirteenth embodiment, a single opening 94 having a greater opening area than the counterpart of the eleventh embodiment can be provided at a boundary between the projection 91 and the probe 3.

Figure 24:
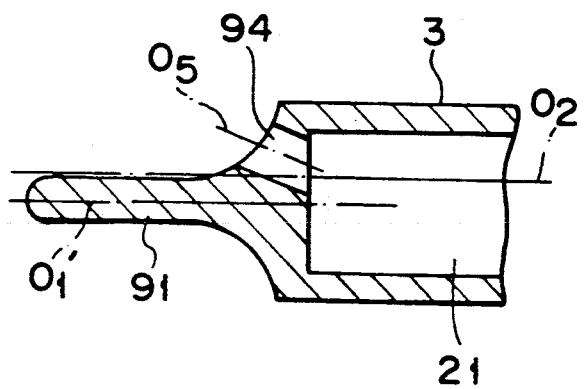
FIG. 24 is an enlarged view, in cross-section, showing a fourteenth embodiment of the present invention.

FIG. 24 shows a fourteenth embodiment of the present invention.

In the fourteenth embodiment, the center axis $O_5$ of the opening 94 at the thirteenth embodiment (FIG. 23) is diagonally intersected on a center axis $O_2$ of the probe 3 in which case it is possible to enlarge the opening area of the opening 94.

The present invention is not restricted to the aforementioned embodiment. For example, the projection 91 may have its distal end so formed as to have a blunt configuration, surgical knife configuration or a serrated configuration.

Various modifications of a distal end configuration of a probe in the diagnostic apparatus will be set forth below.

Figure 25:
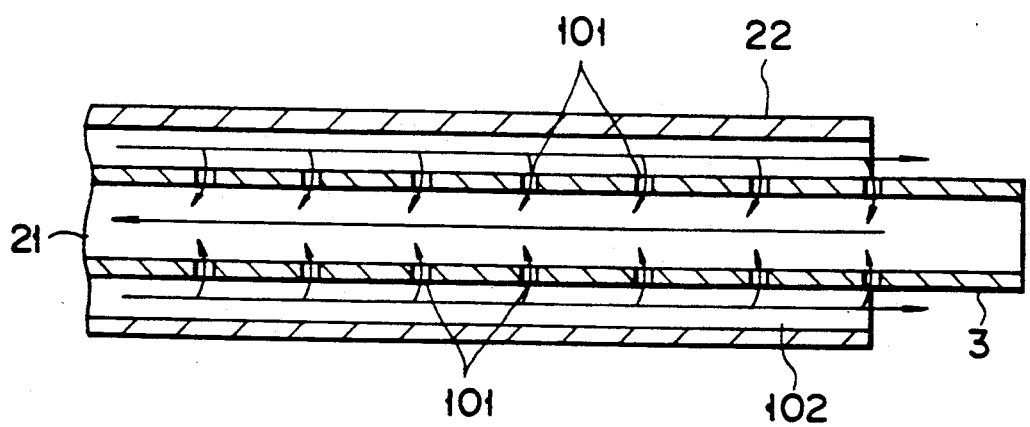

In a modification shown in FIG. 25, a large number of holes 101 are provided substantially at an equal interval and diameter in an axial length of a probe 3. Further, a liquid supply passage 102 is formed at a spacing between the probe 3 and a sheath 22 surrounding the probe 3 with the liquid supply passage 102 communicating with a suction hole 21 (a tubular hole) of the probe 3 via the holes 101 of the probe 3.

In this modification, when a larger quantity of water is supplied through the liquid supply passage 102, some of it can be drawn via the holes 101 into a suction passage 21, thus reducing that quantity of water which is released via the opening of the distal end of the sheath 22. It is thus possible to prevent an accumulation of too much of water, or the flushing of water, in a body cavity of a human being and hence to prevent a lowered field of vision and a subsequent inefficient diagnostic treatment.

Figure 26:
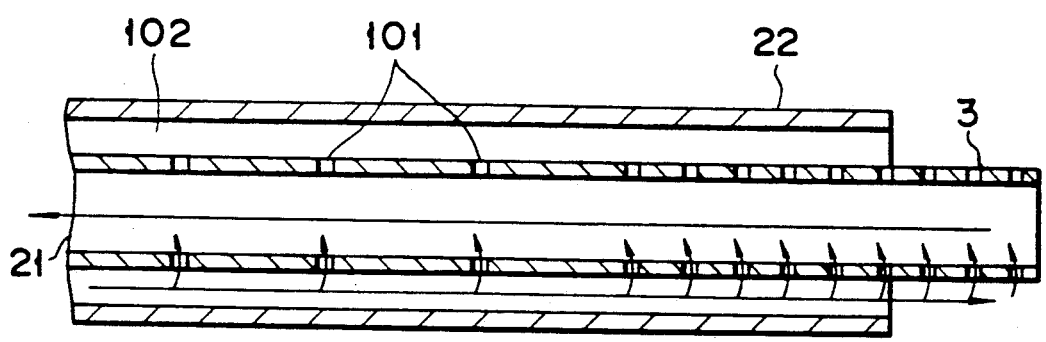

FIG. 26 shows another modification in which a larger number of holes 101 are provided at varied intervals in the wall of a probe 3, that is, at a closer density toward the distal end of the probe 3 than at the other section of the probe 3. As a result, more water is drawn into a water suction passage 21 as the water is moved toward the distal end of the probe 3. It is possible to secure a proper quantity of water up to the distal end of the probe 3 and hence to uniformly cool the probe 3 throughout a whole length.

Figure 27:
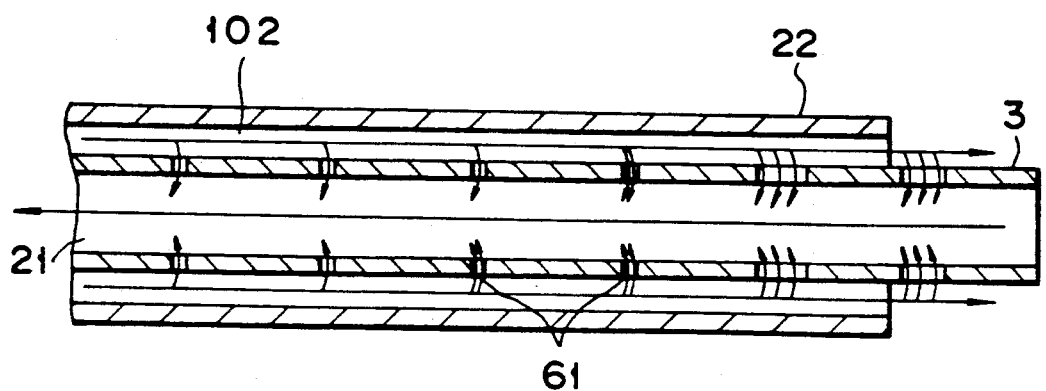

FIG. 27 shows another modification in which a larger number of holes 101 are provided at a substantially equal interval in an axial wall of a probe 3. In this modification, the diameters of the holes 101 are increased toward a distal end of the probe 3. In this modification, more water is drawn into water suction passage 21 as water is moved toward the distal end of the probe 3. This modification can obtain the same advantages as those set forth above in connection with the preceding modification.

Figure 28:
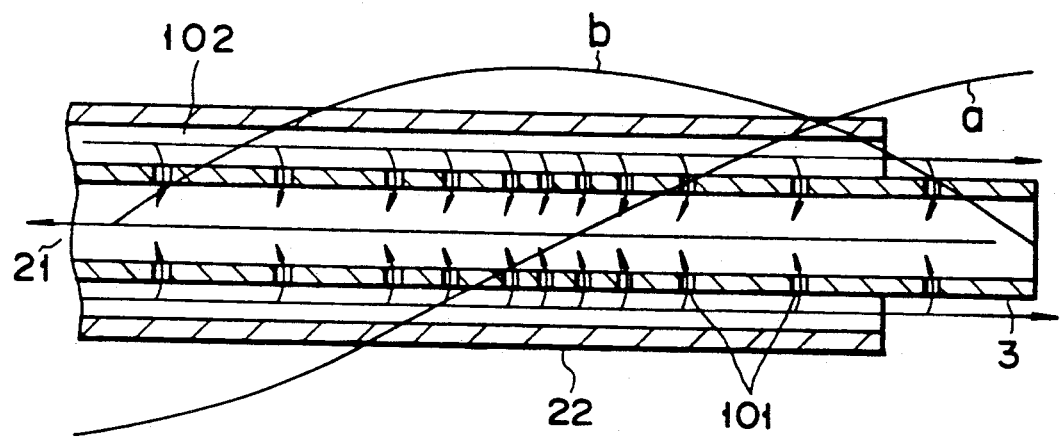

FIG. 28 shows a modification in which a larger number of holes 101 are provided in an axial wall of a probe 3 with more holes 101 arranged at a higher density substantially at an ultrasonic oscillation wave's node than in those areas not including the node. In FIG. 28, a represents the amplitude of the oscillation wave and b a stress distribution of the probe 3.

This arrangement efficiently absorbs a heat generation resulting from a stress at and near the probe's node and hence prevents temperature rise.

A hole 101 of a greater size may be provided substantially at the node of the probe 3 instead of such denser array of holes 101 as shown in FIG. 28. A larger number of holes 101 having a larger size may be provided at a higher density substantially at the node of the probe 3.

Figure 29:
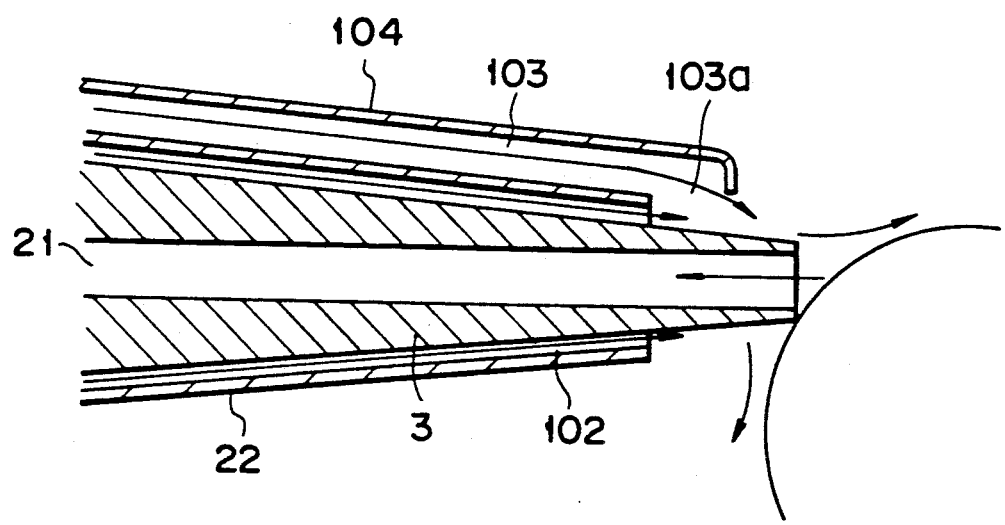

FIG. 29 shows another modification in which a water supply passage 102 is formed between the probe 3 and a covering sheath 22, and a member 104 is provided outside the sheath 22 to provide a gas supply passage 103 along the water supply passage 102. In the modification of FIG. 29, the distal end 103a of the gas supply passage 103 is opened toward the side edge of the distal end of a probe 3. The probe 3, sheath 22 and member 104 have their distal ends all tapered toward a center axis of the probe 3.

According to the present invention, it is possible to cool a water stream in the water supply passage 102, and hence to cool the probe 3, because the gas supply passage 103 is provided outside the sheath 22. Further, water intruding into a visual field of observation is displaced away from that site to provide a better field of observation.

It is also possible to secure a clean field of vision at a region of interest of a human being because the distal end portions of the probe 3, sheath 22 and member 104 are all formed as a tapered end portion each.

FIGS. 30 and 31 show another modification in which water passages 111 and suction passages 112 are provided, as many sets, in the axial wall of a sheath 22 for covering a probe 3. In this modification, the forward end of the water supply passage 111 communicates with that of the associated suction passage 112 to draw a stream of cooling water through the suction passage 112. A water supply passage 102 is also formed in a spacing between the probe 3 and the sheath 22.

This arrangement can cool the sheath 22 per se because the water supply passages 111 and suction passages 112 are provided as many combination sets. It is thus possible to prevent heat which is generated at the probe 3 from being transmitted to an outside.

FIG. 32 shows another modification of the present invention. In this modification, a water passage 111 and suction passage 112 are helically provided with the center axis of a sheath 22 as a center. The forward end of the water supply passage 111 communicates with that of the suction passage 112. A cooling water stream in the water supply passage 111 is drawn through the suction passage 112. A water supply passage 102 is formed in a spacing between a probe 3 and the sheath 22.

The sheath 22 per se can be cooled by the water supply passage 111 and suction passage 112 providing a spiral array. It is possible to prevent heat which is evolved at the probe 3 from being transmitted to an outside.

FIG. 33 shows another modification of the present invention. In the modification shown in FIG. 33, a water supply tube 122 is provided, as a water supply passage 121, in a hollow hole of a probe 3. A suction passage 123 is provided between the probe 3 and the water supply tube 122. A sheath 22 is provided outside the probe 3 and a second water supply passage 124 is formed between the probe 3 and the sheath 22. The water supply tube 122 is made shorter in length than the probe 3 as viewed from the distal end of the probe.

According to this modification, some of a water stream in the water supply passage 121 of the probe 3 can be drawn through the suction passage 122. A larger amount of water need not be supplied toward a visual field of observation at the distal end of the probe 3, ensuring a better field of observation.

Figure 34:
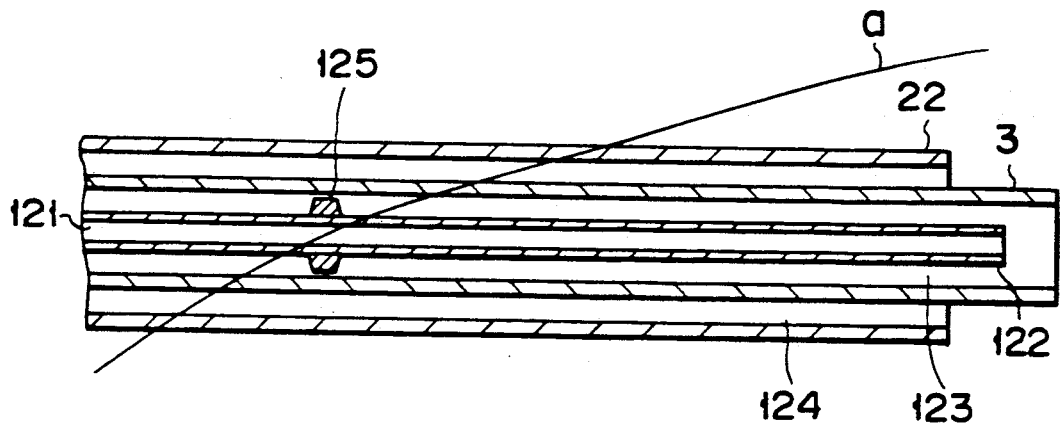
Figure 35:
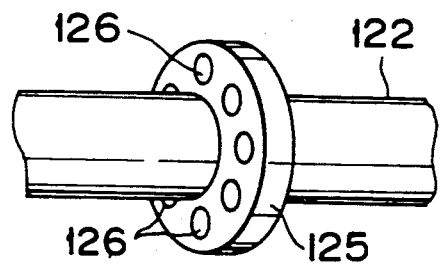
FIGS. 35 and 36, each, are a diagonal view showing a different modification of the above apparatus having a flange for supporting a water supply tube.

FIGS. 34 and 35 show another modification of FIG. 33. In the arrangement shown in FIGS. 34 and 35, a flange 125 is provided partway on a water supply tube 122 such that it supports the supply tube 122 at an axial center of the probe 125. The flange 125 is located substantially at the oscillation wave's node of the probe 3 and has a larger number of through holes 126 as shown in FIG. 35 to provide passages.

Figure 36:
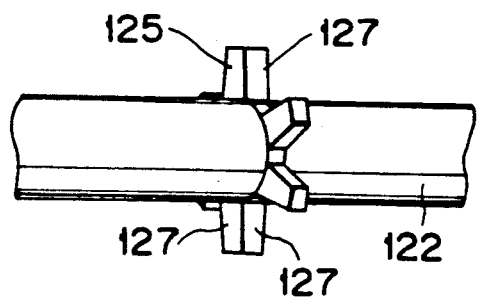

A larger number of grooves 127 may be provided, as shown in FIG. 36, in a flange 125 in place of through holes 126 of the flange shown in FIG. 35 to provide passages.

FIG. 37 shows another embodiment of the present invention. In this embodiment, the hole of a probe 3 provides a suction passage 131 and a helical water supply tube 132 is arranged in a suction passage 131 of the probe 3 in a concentric fashion. A second water supply passage 133 may be provided between the probe 3 and a sheath 22.

The distal end of the water supply tube 132 is located in the suction passage 131 at a location short of the distal end of the probe 3, that is, without being projected from the distal end of the probe 3.

This arrangement allows some of water which is supplied from the water supply tube 132 to be drawn through the suction passage 131, obviating the need of supplying more water toward a visual field of observation. It is possible to secure better field of observation. Further, the length of the water supply tube 132 can be adjusted in accordance with the length of the probe 3, because the water supply tube 132 has such a helical structure as shown in FIG. 37.

FIG. 38 shows another modification of the present invention. This modification is similar to the modification 33 except that a water supply tube 122 has a larger number of water supply holes 141.

This arrangement can uniformly cool a probe 3 as a whole.

The arrangement as set out above can be applied to those having a water supply passage in a probe 3.

The present invention is not restricted to those as set forth above. Various changes and modifications of the present invention may be made without departing from the spirit and scope of the present invention.

What is claimed is:

1. An ultrasound type treatment apparatus comprising:
   ultrasonic oscillation means for outputting an ultrasonic oscillation wave, said ultrasonic oscillation means having an input terminal;
   drive means for driving said ultrasonic oscillation means;

ultrasonic wave transmitting means, connected to said ultrasonic oscillation means, for transmitting the ultrasonic oscillation wave from the oscillation wave means to an affected region of interest of a human being;

communicating means formed around the ultrasonic wave transmitting means, through which cooling medium is passed;

supply means for supplying the cooling medium to said communicating means, monitor means for monitoring a drive state of said ultrasonic oscillation means and outputting monitor information;

determining means for receiving the monitor information from the monitor means and for determining whether or not the supply of the cooling medium to said communicating means is normal; and control means for stopping a drive of the ultrasonic oscillation means when said determining means determines that the supply of the cooling medium is not normal.

2. An apparatus according to claim 1, wherein said drive means comprises:

a drive circuit having an output terminal and generating a drive signal; and an output transformer having a primary winding connected to the output terminal of said drive circuit and a secondary winding connected to the input terminal of said ultrasonic oscillation means, said monitor means comprises: a resistor connected in parallel with the primary winding of said output transformer;

a first rectifying circuit for rectifying a voltage generated across said resistor and producing an output voltage, the output voltage of said first rectifying circuit corresponding to a voltage (V) applied to said ultrasonic oscillation means;

a current detector interposed between the primary winding of said output transformer and said drive circuit and generating a voltage;

a second rectifying circuit for rectifying the voltage generated in said current detector and generating an output voltage, the output voltage of said second rectifying circuit corresponding to a current (I) flowing in said ultrasonic oscillation means, and an arithmetic operation circuit, connected between said first and second rectifying circuits and, for computing an impedance (Z) by dividing the output voltage of said first rectifying circuit by the output voltage of said second rectifying circuit and for outputting a voltage corresponding to the impedance, and said determining means comprises (Z):

reference value setting means for generating a reference value ($Z_o$) of the impedance (Z) of said ultrasonic oscillation means, the reference value ($Z_o$) providing a reference base for determining a state of supply of the cooling medium; and a comparator having an inverting input terminal (−) connected to said arithmetic operation circuit and a non-inverting input terminal (+) connected to said reference value setting means and adapted to compare a detection value, corresponding to the impedance (Z) of said ultrasonic oscillation means, received from said arithmetic operation circuit with the reference value ($Z_o$) received from said reference value setting means.

3. An apparatus according to claim 1, wherein said driving means comprises:

a drive circuit having an output terminal and generating a drive signal; and an output transformer having a primary winding connected to the output terminal of said drive circuit and a secondary winding connected to the input terminal of said ultrasonic oscillation means, said monitor means comprises:

a resistor connected in parallel with the primary winding of said output transformer;

a rectifying circuit for rectifying a voltage generated across the resistor and producing an output voltage, the output voltage of said rectifying circuit corresponding to a voltage (V) applied to said ultrasonic oscillation means;

detective means for detecting an oscillation amplitude (A) of said ultrasonic oscillation means;

an oscillation detector for outputting a voltage corresponding to the oscillation amplitude (A) of said ultrasonic oscillation means which is detected by said detective means; and an arithmetic operation circuit for outputting a signal corresponding to a calculation value (S) obtained by dividing the output voltage of said oscillation detector by the output voltage of said rectifying circuit, and said determining means comprises:

reference value setting means for generating a reference value ($S_o$) corresponding to the calculation value (S) supplied from said arithmetic operation circuit, the reference value ($S_o$) providing a reference base for determining a state of supply of the cooling medium; and a comparator having an inverting input terminal (−) connected to said arithmetic operation circuit and a non-inverting input terminal (+) connected to said reference value ($S_o$) setting means and adapted to compare an output signal corresponding to the calculation value (S) supplied from said arithmetic operation circuit with the reference value ($S_o$) supplied from said arithmetic operation means.

4. An apparatus according to claim 1, wherein said drive means comprises:

a drive circuit having an output terminal and generating a drive signal; and an output transformer having a primary winding connected to the output terminal of said drive circuit and a secondary winding connected to the input terminal of said ultrasonic oscillation means;

said monitor means comprises:

a wattmeter for detecting a dissipation power (P) of said ultrasonic oscillation means and for outputting a voltage corresponding to a result of detection;

detective means for detecting an oscillation amplitude (A) of said ultrasonic oscillation means;

an oscillation detector for outputting a voltage corresponding to the oscillation amplitude (A) of said ultrasonic oscillation means detected by said detective means; and an arithmetic operation circuit for outputting a signal corresponding to a calculation value (T) obtained by dividing the output voltage of said oscillation detector by the output voltage of said wattmeter, said determining means comprises:

reference value setting means for generating a reference value ($T_o$) corresponding to the calculation value (T) supplied from said arithmetic operation circuit, the reference value ($T_o$) providing a reference base for determining a state of supply of the cooling medium; and a comparator having an inverting input terminal (−) connected to said arithmetic operation circuit and a non-inverting input terminal (+) connected to said reference value setting means and adapted to compare an output signal corresponding to the calculation value (T) of said arithmetic operation circuit with the reference value ($T_o$) supplied from said reference value setting means.

5. An apparatus according to claim 1, wherein said drive means comprises:

a constant current power source circuit connected to a commercial power source to supply a constant current;

a drive circuit having an input terminal connected to said constant current power source circuit and having an output terminal to generate a drive signal; and an output transformer having a primary winding connected to the output terminal of said drive circuit and a secondary winding connected to the input terminal of said ultrasonic oscillation means, said monitor means comprises:

a current detector provided on a connection line between said constant current power source circuit and said drive circuit, an output of said current detector corresponding to a constant current (I');

a resistor connected in parallel with the primary winding of said output transformer;

a rectifying circuit for rectifying a voltage generated across said resistor and producing an output voltage, the output voltage of said rectifying circuit corresponding to a voltage (V) applied to said ultrasonic oscillation means; and an arithmetic operation circuit for outputting an output signal corresponding to a calculation value (U) obtained by dividing the output voltage of said current detector by the output voltage of said rectifying circuit, and said determining means comprises:

reference value setting means for generating a reference value ($U_o$) corresponding to the calculation value (U) supplied from said arithmetic operation circuit, the reference value ($U_o$) providing a reference base for determining a state of supply of the cooling medium; and a comparator having an inverting input terminal (−) connected to said arithmetic operation circuit and a non-inverting input terminal (+) connected to said reference value setting means and adapted to compare an output signal corresponding to the calculation value (U) supplied from the arithmetic operation circuit with the reference value ($U_o$) supplied from said reference value setting means.

6. An apparatus according to claim 1, wherein said communicating means includes a tubular sheath covering said ultrasonic wave transmitting means to define a spacing relative to said ultrasonic wave transmitting means and said tubular sheath having a proximal end extending toward said ultrasonic oscillation means and a distal end extending toward a distal end of said ultrasonic wave transmitting means, cooling medium supply means being provided between said sheath and said ultrasonic wave transmitting means to allow cooling medium to flow through the spacing.

7. An apparatus according to claim 6, wherein said ultrasonic wave transmitting means defines a hole therein and has a probe serving as a first suction passage provided by the hole and said sheath includes an inner tubular sheath section covering said probe to define a spacing relative to said probe and an outer sheath section providing a spacing relative to said inner sheath section, a cooling medium supply passage and a second suction passage being such that one of them is provided between said probe and said inner sheath section, and the other between said inner sheath section and said outer sheath section.

8. An apparatus according to claim 7, wherein communication means is provided at a distal end of said inner section at a location short of a distal end of said outer sheath section to allow a fluid communication to be achieved between said cooling medium supply passage and said second suction passage.

9. An apparatus according to claim 8, wherein said sheath defines said second suction passage as a spacing between said inner sheath section and said probe, and said cooling medium supply passage as a spacing between said outer sheath section and said inner sheath section.

10. An apparatus according to claim 9, wherein said sheath has an end wall for closing a gap provided between a distal end of said inner sheath section and that of said outer sheath section, and cooling medium supply means is provided between said cooling medium supply passage and said second suction passage to achieve communication between the two.

11. An apparatus according to claim 8, wherein said sheath provides said cooling medium supply passage as a spacing between said inner sheath section and said probe and said suction path as a spacing between said outer sheath section and said inner sheath section 12. An apparatus according to claim 11, wherein a cover flange is provided integral with a distal end of said outer sheath section and extends toward said probe to provide a constriction open gap at the distal end of said outer sheath section to allow a suction function to be enhanced toward said second suction passage, said constriction open gap allowing a supply of cooling medium between said cover flange and an outer periphery of said probe.

13. An apparatus according to claim 8, wherein said sheath is so formed that an inner cooling medium supply passage is provided between said probe and said inner sheath section, and an outer cooling medium supply passage between said inner sheath section and said outer sheath section, a cover flange is provided integral with a distal end of said inner sheath section and extends toward said probe to provide an open gap for substantially closing said cooling medium supply passage, and communication means is provided at the distal end portion of said probe to allow a communication to be achieved between said suction passage and said cooling medium supply passage.

14. An apparatus according to claim 11, wherein said probe has suction means provided at a proximal end portion to allow a communication to be achieved between said second suction path and said first suction passage.

15. An apparatus according to claim 14, further comprising a handpiece covering an outer periphery of said ultrasonic oscillation means to define a cooling medium passage communicating with said cooling medium supply passage.

16. An apparatus according to claim 7, wherein a projection is provided integral with a distal end of said probe with its base end set greater in thickness than its distal end and communication means is provided near the base end of said projection to allow a fluid communication with said first suction passage.

17. An apparatus according to claim 16, wherein said communication means has a pair of openings, one at each side of said base end portion of said projection with their center axes intersected on a center axis of said probe.

18. An ultrasound type treatment apparatus comprising:

ultrasonic oscillation means for outputting an ultrasonic oscillation wave;

ultrasonic wave transmitting means, connected to said ultrasonic wave oscillation means, for transmitting the ultrasonic oscillation wave from said oscillation means to an affected region of interest in a patient;

communicating means, formed around said ultrasonic wave transmitting means; and supply means for supplying a cooling medium to said communicating means;

wherein said ultrasonic wave transmitting means defines a hole therein and comprises a probe using said hole as a first suction passage;

said communicating means including an inner tubular sheath section covering said probe so as to define a space relative to said probe, and an outer tubular sheath section covering said inner sheath section so as to define a space relative to said inner sheath section, said inner sheath section having both a proximal end portion extending toward said ultrasonic oscillation means and a distal end portion extending toward a distal end of said probe, said outer sheath section having both a proximal end portion extending toward said ultrasonic oscillation means and a distal end portion extending toward the distal end of said probe; and a cooling medium supply passage and a second suction passage are provided, with one being between said probe and said inner sheath section, and the other being between said inner sheath section and said outer sheath section, said cooling medium supply supply passage and said second suction passage forming a cooling medium transmitting means.

19. An apparatus according to claim 18, wherein communication means is provided at a distal end of said inner sheath section at a location short of a distal end of said outer sheath section to allow a fluid communication to be achieved between said cooling medium supply passage and said second suction passage.

20. An apparatus according to claim 18, wherein a projection is provided integral with a distal end of said probe with its base end set greater in thickness than its distal end, and communication means is provided near the base end of said projection to allow fluid communication with said first suction passage.

* * * * *